(12) United States Patent
Sävmarker et al.

(10) Patent No.: US 12,303,472 B2
(45) Date of Patent: May 20, 2025

(54) PHARMACEUTICAL DEVICE FOR USE IN INTRANASAL ADMINISTRATION

(71) Applicant: OREXO AB, Uppsala (SE)

(72) Inventors: Jonas Sävmarker, Uppsala (SE); Robert Rönn, Uppsala (SE)

(73) Assignee: OREXO AB, Uppsala (SE)

( * ) Notice: Subject to any disclaimer, the term of this patent is extended or adjusted under 35 U.S.C. 154(b) by 0 days.

(21) Appl. No.: 18/323,115

(22) Filed: May 24, 2023

(65) Prior Publication Data

US 2023/0310349 A1    Oct. 5, 2023

Related U.S. Application Data

(63) Continuation of application No. PCT/GB2022/052983, filed on Nov. 25, 2022.

(30) Foreign Application Priority Data

Nov. 25, 2021    (GB) ..................................... 2117016

(51) Int. Cl.
    *A61K 31/137*    (2006.01)
    *A61K 9/00*      (2006.01)
    *A61K 47/26*     (2006.01)
    *A61K 47/36*     (2006.01)

(52) U.S. Cl.
    CPC .......... *A61K 31/137* (2013.01); *A61K 9/0043* (2013.01); *A61K 9/0075* (2013.01); *A61K 47/26* (2013.01); *A61K 47/36* (2013.01)

(58) Field of Classification Search
    CPC .... A61K 31/137; A61K 9/0043; A61K 47/26; A61K 45/06; A61K 31/277; A61K 31/417; A61K 9/08; A61K 2300/00; A61K 31/485; A61K 47/02; A61K 31/7016; A61K 47/10; A61K 47/12; A61K 47/183; A61K 47/186; A61K 9/0048; A61K 9/0056; A61K 9/006; A61K 31/439; A61K 9/14; A61K 9/145; A61K 9/146; A61K 38/095; A61K 47/38; A61K 9/0075; A61K 38/08; A61K 47/36; A61K 9/1623; A61K 9/1652; A61K 9/1694; A61P 37/08; A61P 27/14; A61P 11/00; A61P 11/06; A61P 11/08; A61P 11/16; A61P 17/04; A61P 37/06; A61P 43/00; A61P 7/00; A61P 9/02; A61P 9/04; A61P 37/00; A61M 15/08; A61M 2202/064; A61M 15/0045; A61M 15/0068; A61M 11/02; A61M 15/0028; A61M 2202/0007; A61M 15/0091; A61M 15/0021; A61M 15/0035; A61M 15/0041; A61M 15/0086; A61M 2202/06; A61M 2206/16; A61M 2209/02
    See application file for complete search history.

(56) References Cited

U.S. PATENT DOCUMENTS

| | | |
|---|---|---|
| 5,082,669 A | 1/1992 | Shirai et al. |
| 5,702,362 A | 12/1997 | Herold et al. |
| 6,398,074 B1 | 6/2002 | Bruna et al. |
| 6,938,798 B2 | 9/2005 | Stradella |
| 7,722,566 B2 | 5/2010 | Tsutsui |
| 7,947,742 B2 | 5/2011 | Batycky et al. |
| 8,415,397 B2 | 4/2013 | Batycky et al. |
| 8,747,813 B2 | 6/2014 | Batycky et al. |
| 9,724,713 B2 | 8/2017 | Baillet et al. |
| 9,789,071 B2 | 10/2017 | Fleming |
| 9,895,444 B2 | 2/2018 | Maggio |
| 10,039,710 B2 | 8/2018 | Potta et al. |

(Continued)

FOREIGN PATENT DOCUMENTS

| | | | | |
|---|---|---|---|---|
| AU | 2006207868 A1 | * | 9/2006 | ............... A61K 9/16 |
| CN | 1565451 | | 1/2005 | |

(Continued)

OTHER PUBLICATIONS

Del Valle, "Cyclodextrins and Their Uses: A Review," Process Biochemistry 39:1033-1046 (2004).

(Continued)

*Primary Examiner* — Audrea B Coniglio
(74) *Attorney, Agent, or Firm* — Troutman Pepper Lock LLP (Rochester)

(57) ABSTRACT

Disclosed is a needle-free applicator that is suitable for administering a solid, amorphous, mono-particulate powder composition into a body cavity of a human patient, which cavity includes a mucosal surface, wherein the applicator comprises:

(i) an opaque reservoir comprising said powder composition;

(ii) an optional actuating means for generating a force upon actuation of the device by a user; and (iii) a dispensing means through which, following said actuation, said powder composition may be dispensed, wherein said powder composition comprises a pharmacologically-effective dosage amount of an adrenergic receptor modulator, or a pharmaceutically-acceptable salt thereof, encapsulated in an amorphous state along with a pharmaceutically-acceptable carrier material; and which powder composition is less than about 4% chemically degraded after storage for:

(a) at least about 3 months at 40° C. and 75% relative humidity; and/or (b) at least about 18 months at below about 30° C.; and/or (c) at least about 18 hours at above about 1 million lux of UV light.

30 Claims, 4 Drawing Sheets

(56) References Cited

U.S. PATENT DOCUMENTS

| | | | |
|---|---|---|---|
| 10,624,864 B2 | 4/2020 | Sanghvi et al. | |
| 10,653,690 B1 | 5/2020 | Sävmarker et al. | |
| 10,688,044 B2 | 6/2020 | Hartman et al. | |
| 10,729,687 B1 | 8/2020 | Sävmarker et al. | |
| 10,792,253 B2 | 10/2020 | Haruta | |
| 10,898,480 B1 | 1/2021 | Sävmarker et al. | |
| 11,077,075 B2 | 8/2021 | Narayanan et al. | |
| 11,400,045 B2 | 8/2022 | Temtsin-Krayz et al. | |
| 11,737,980 B2 * | 8/2023 | Sävmarker | A61K 31/485 424/499 |
| 11,957,647 B2 * | 4/2024 | Sävmarker | A61K 9/1652 |
| 2005/0019411 A1 | 1/2005 | Colombo et al. | |
| 2005/0042178 A1 | 2/2005 | Trunk et al. | |
| 2005/0118272 A1 | 6/2005 | Besse et al. | |
| 2007/0202163 A1 | 8/2007 | Rawas-Qalaji et al. | |
| 2008/0269347 A1 | 10/2008 | Bruss et al. | |
| 2009/0264530 A1 | 10/2009 | Nickell | |
| 2011/0045088 A1 | 2/2011 | Tsutsui et al. | |
| 2013/0213398 A1 | 8/2013 | Lipp et al. | |
| 2015/0005356 A1 * | 1/2015 | Fleming | A61K 31/137 514/521 |
| 2015/0018379 A1 | 1/2015 | Strang et al. | |
| 2015/0320695 A1 | 11/2015 | Ryoo et al. | |
| 2016/0045474 A1 | 2/2016 | Gandhi et al. | |
| 2016/0166503 A1 | 6/2016 | Crystal et al. | |
| 2016/0235687 A1 | 8/2016 | Prajapati et al. | |
| 2016/0374966 A1 | 12/2016 | Rawas-Qalaji et al. | |
| 2017/0014341 A1 | 1/2017 | Armer et al. | |
| 2017/0071850 A1 | 3/2017 | Vehring et al. | |
| 2017/0071851 A1 | 3/2017 | Keegan et al. | |
| 2017/0119699 A1 | 5/2017 | Batycky et al. | |
| 2017/0319509 A1 | 11/2017 | Canal et al. | |
| 2018/0092839 A1 | 4/2018 | Gooberman | |
| 2018/0193332 A1 | 7/2018 | Loughlin et al. | |
| 2019/0008759 A1 | 1/2019 | Rubin | |
| 2019/0070105 A1 | 3/2019 | Amancha et al. | |
| 2019/0307156 A1 * | 10/2019 | Zasypkin | A23P 10/35 |
| 2020/0316324 A1 | 10/2020 | Hrkach | |
| 2022/0087938 A1 | 3/2022 | Sävmarker et al. | |
| 2022/0395457 A1 | 12/2022 | Lyman et al. | |
| 2023/0355552 A1 | 11/2023 | Sävmarker et al. | |
| 2024/0024244 A1 | 1/2024 | Sävmarker et al. | |

FOREIGN PATENT DOCUMENTS

| | | | | |
|---|---|---|---|---|
| CN | 1615867 | | 5/2005 | |
| CN | 1640402 | | 7/2005 | |
| CN | 1781479 | A | 6/2006 | |
| CN | 1813739 | | 8/2006 | |
| CN | 1939358 | A | 4/2007 | |
| CN | 104547220 | A | 4/2015 | |
| EP | 0 657 176 | A2 | 6/1995 | |
| EP | 0 736 299 | A1 | 10/1996 | |
| EP | 1 093 818 | A1 | 4/2001 | |
| EP | 1349598 | B1 * | 11/2004 | A61M 15/00 |
| EP | 2251038 | A1 | 11/2010 | |
| EP | 3 025 705 | A1 | 6/2016 | |
| GB | 1 287 475 | | 8/1972 | |
| JP | 2000178184 | A | 6/2000 | |
| WO | 91/09592 | A1 | 7/1991 | |
| WO | 00/62757 | A1 | 10/2000 | |
| WO | 01/30288 | A1 | 5/2001 | |
| WO | 01/60338 | A1 | 8/2001 | |
| WO | 01/87264 | A2 | 11/2001 | |
| WO | 01/89485 | A1 | 11/2001 | |
| WO | 02/047607 | A2 | 6/2002 | |
| WO | 2003/061632 | A1 | 7/2003 | |
| WO | 2004/054511 | A2 | 7/2004 | |
| WO | 2004/075877 | A1 | 9/2004 | |
| WO | 2004/100857 | A2 | 11/2004 | |
| WO | 2004/112702 | A2 | 12/2004 | |
| WO | 2005/044186 | A2 | 5/2005 | |
| WO | 2005/065652 | A1 | 7/2005 | |
| WO | 2005/079777 | A1 | 9/2005 | |
| WO | 2006/085101 | A2 | 8/2006 | |
| WO | 2006/101536 | A1 | 9/2006 | |
| WO | 2007024123 | A1 | 3/2007 | |
| WO | 2007/086039 | A1 | 8/2007 | |
| WO | 2007/096906 | A2 | 8/2007 | |
| WO | 2007/108010 | A2 | 9/2007 | |
| WO | 2007/113856 | A2 | 10/2007 | |
| WO | 2008/033023 | A2 | 3/2008 | |
| WO | 2008/127746 | A1 | 10/2008 | |
| WO | 2009/040595 | A1 | 4/2009 | |
| WO | 2009/120735 | A1 | 10/2009 | |
| WO | 2010/135495 | A2 | 11/2010 | |
| WO | 2010/142696 | A1 | 12/2010 | |
| WO | 2010/144865 | A2 | 12/2010 | |
| WO | 2011/036521 | A2 | 3/2011 | |
| WO | 2012/027731 | A2 | 3/2012 | |
| WO | 2012/042224 | A2 | 4/2012 | |
| WO | 2012/075455 | A2 | 6/2012 | |
| WO | 2012/109694 | A1 | 8/2012 | |
| WO | 2013/168437 | A1 | 11/2013 | |
| WO | 2014/004400 | A2 | 1/2014 | |
| WO | 2015/034822 | A1 | 3/2015 | |
| WO | 2015/091365 | A1 | 6/2015 | |
| WO | 2015/095389 | A1 | 6/2015 | |
| WO | 2015/095644 | A1 | 6/2015 | |
| WO | 2016/016431 | A1 | 2/2016 | |
| WO | WO2016/044813 | A1 * | 3/2016 | A61K 9/107 |
| WO | 2016/055544 | A1 | 4/2016 | |
| WO | 2016/133863 | A1 | 8/2016 | |
| WO | 2016/161501 | A1 | 10/2016 | |
| WO | 2016/179026 | A1 | 11/2016 | |
| WO | 2017/127641 | A1 | 7/2017 | |
| WO | 2017/144636 | A1 | 8/2017 | |
| WO | 2017/158439 | A1 | 9/2017 | |
| WO | 2017/189947 | A1 | 11/2017 | |
| WO | 2017/208209 | A1 | 12/2017 | |
| WO | 2017/218918 | A1 | 12/2017 | |
| WO | 2018/064377 | A1 | 4/2018 | |
| WO | 2018/064672 | A1 | 4/2018 | |
| WO | 2018/089709 | A1 | 5/2018 | |
| WO | 2018/093666 | A1 | 5/2018 | |
| WO | 2018/148382 | A1 | 8/2018 | |
| WO | 2018/195029 | A1 | 10/2018 | |
| WO | 2019/038756 | A1 | 2/2019 | |
| WO | 2019/157099 | A1 | 8/2019 | |
| WO | 2019/241401 | A1 | 12/2019 | |
| WO | 2020/205663 | A1 | 10/2020 | |
| WO | WO2021/005325 | A1 * | 1/2021 | A61K 9/16 |
| WO | 2021/234366 | A1 | 11/2021 | |

OTHER PUBLICATIONS

Per Gisle Djupesland, "Nasal Drug Delivery Devices: Characteristics and Performance in a Clinical Perspective—A Review," Drug Deliv. and Transl. Res. 3:42-62 (2013).

Fasiolo et al., "Opportunity and Challenges of Nasal Powders: Drug Formulation and Delivery," Eur. J. Pharm. Sci. 113:2-17 (2018).

Florence et al., "The Economic Burden of Prescription Opioid Overdose, Abuse and Dependence in the United States, 2013," Med Care 54(10):901-906 (2016).

Górska et al., "The Influence of Trehalose-Maltodextrin and Lactose-Maltodextrin Matrices on Thermal and Sorption Properties of Spray-Dried β-Lactoglobulin-Vitamin D3 Complexes," J. Therm. Anal. Calorim. 112:429-436 (2013).

Hahn & Sucker, "Solid Surfactant Solutions of Active Ingredients in Sugar Esters," Pharm. Res. 6(11):958-960 (1989).

Jüptner et al., "Spray Dried Formulations for Nasal Applications-Challenges and Opportunities in Filling and Drug Delivery," Respiratory Drug Delivery 2:345-348 (2018).

Kürti et al., "The Effect of Sucrose Esters on a Culture Model of the Nasal Barrier," Toxicology in Vitro 26:445-454 (2012).

Li et al., "Non-Ionic Surfactants as Novel Intranasal Absorption Enhancers: In Vitro and In Vivo Characterization," Drug Delivery 23(7):2272-2279 (2016).

Middleton et al., "The Pharmacodynamic and Pharmacokinetic Profile of Intranasal Crushed Buprenorphine and Buprenorphine/Naloxone Tablets in Opioid Abusers," Addiction 106:1460-1473 (2011).

(56) References Cited

OTHER PUBLICATIONS

Momin et al., "Investigation Into Alternative Sugars as Potential Carriers for Dry Powder Formulation of Budesonide," BioImpacts 1(2):105-111 (2011).
Naini et al., "Physicochemical Stability of Crystalline Sugars and Their Spray-Dried Forms: Dependence Upon Relative Humidity and Suitability for Use in Powder Inhalers," Drug Development and Industrial Pharmacy 24(10):895-909(1998).
Pozzoli et al., "Dry Powder Nasal Drug Delivery: Challenges, Opportunities and a Study of the Commercial Teijin Puvlizer Rhinocort Device and Formulation," Drug Development and Industrial Pharmacy 42(10):1660-1668 (2016).
Pozzoli et al., "Development of a Soluplus Budesonide Freeze-Dried Powder for Nasal Drug Delivery," Drug Development and Industrial Pharmacy 43(9):1510-1518 (2017).
Prekupec et al., "Misuse of Novel Synthetic Opioids: A Deadly New Trend," J. Addic. Med. 11(4):256-265 (2017).
Rudd et al., "Increases in Drug and Opioid-Involved Overdose Deaths - United States, 2010-2015," Morbidity and Mortality Weekly Report 65(50-51):1445-1452 (2016).
Russo et al., "Primary Microparticles and Agglomerates of Morphine for Nasal Insufflation," J. Pharm. Sci. 95(12):2553-2561 (2006).
Sacchetti et al., "Caffeine Microparticles for Nasal Administration Obtained by Spray Drying," Int. J. Pharm. 242:335-339 (2002).
Saokham and Loftsson, "γ-Cyclodextrin," Int. J. Pharm. 516:278-292 (2017).
Szüts and Szabó-Révész, "Sucrose Esters as Natural Surfactants in Drug Delivery Systems-A Mini-Review," Int. J. Pharm. 433:1-9 (2012).
Valdés et al., "Physicochemical Characterization and Cytotoxic Studies of Nonionic Surfactant Vesicles Using Sucrose Esters as Oral Delivery Systems," Colloids and Surfaces B: Biointerfaces 117:1-6 (2014).
Vengerovich et al., "Analysis of the Efficiency of Microencapsulated Sustained-Release Form of Naloxone on the Experimental Model of Fentanyl Poisoning," Bull. Exp. Biol. Med. 163(6):737-741 (2017).
Zhao et al., "Hydroxypropyl-β-Cyclodextrin as Anti-Hygroscopicity Agent In Amorphous Lactose Carriers for Dry Powder Inhalers," Powder Technology 2-11 (2018).
Barnett et al., "Opioid Antagonists," Journal of Pain and Symptom Management 47(2):341-352 (2014).
Thorat S., "Formulation and Product Development of Nasal Spray: An Overview," Scholars Journal of Applied Medical Sciences 4(8D):2976-2985 (2016).
Oliveira et al., "Spray Drying of Food and Herbal Products," Chapter 5 pp. 113-156 (2010).
Mehta P., "Imagine the Superiority of Dry Powder Inhalers from Carrier Engineering," Journal of Drug Delivery 2018:5635010 (2018).
Dowd et al., "Pharmacology and Therapeutics for Dentistry," p. 319 (2010).
Desobry et al., "Influence of Maltodextrin Systems at an Equivalent 25DE on Encapsulated β-Carotene Loss During Storage," Journal of Food Processing and Preservation 23:39-55 (1999).
Gonnissen et al., "Development of Directly Compressible Powders Via Co-Spray Drying," Eur. J. Pharm. Biopharm. 67:220-226 (2007).
Kumar et al., "Sugars as Bulking Agents to Prevent Nano-Crystal Aggregation During Spray or Freeze-Drying," Int. J. Pharmaceutics 471:303-311 (2014).
Li et al., "Characterization of Mechanical and Encapsulation Properties of Lactose/Maltodextrin/WPI Matrix," Food Hydrocolloids 63:149-159 (2017).
Lucas et al., "Protein Deposition From Dry Powder Inhalers: Fine Particle Multiplets as Performance Modifiers," Pharmaceutical Research 15(4):562-569 (1998).
Masum et al., "Effect of Lactose-to-Maltodextrin Ratio on Emulsion Stability and Physicochemical Properties of Spray-Dried Infant Milk Formula Powders," J. Food Eng. 254:34-41 (2019).
Pedersen et al., "Solid State Characterisation of a Dry Emulsion: A Potential Drug Delivery System," Int. J. Pharm. 171:257-270 (1998).
Tewa-Tagne et al., "Preparation of Redispersible Dry Nanocapsules by Means of Spray-Drying: Development and Characterisation," Eur. J. Pharm. Sci. 30:124-135 (2007).
Shojaei A.H., "Buccal Mucosa as a Route for Systemic Drug Delivery: A Review," J. Pharm. Pharmaceut. Sci. 1(1):15-30 (1998).
Gandhi et al., "Oral Cavity as a Site for Bioadhesive Drug Delivery," Adv. Drug Deliv. Rev. 13:43-74 (1994).
Bertram et al., "In Situ Gelling, Bioadhesive Nasal Inserts for Extended Drug Delivery: In Vitro Characterization of a New Nasal Dosage Form," Eur. J. Pharm. Sci. 27:62-71 (2006).
Kou and Zhou, "Amorphous Solid Dispersions," Chapter 16, Shah et al. (Eds.), Springer (2014).
Branchu et al., "Hydroxypropyl-β-cyclodextrin Inhibits Spray-Drying-Induced Inactivation of β-Galactosidase," J. Pharm. Sci. 88(9):905-911 (1999).
Mazzobre et al., "Protective Role of Trehalose on Thermal Stability of Lactase in Relation to its Glass and Crystal Forming Properties and Effect of Delaying Crystallization," Lebensm.-Wiss. u.-Technol. 30:324-329 (1997.
Amaro et al., "Co-Spray Dried Carbohydrate Microparticles: Crystallisation Delay/Inhibition and Improved Aerosolization Characteristics Through the Incorporation of Hydroxypropyl-β-cyclodextrin with Amorphous Raffinose or Trehalose," Pharm Res. 32:180-195 (2015).
Newman et al., "Assessing the Performance of Amorphous Solid Dispersions," Journal of Pharmaceutical Sciences, 101:1355-1377 (2012).
Alpha-D-Lactose monohydrate product page (2015). Retrieved from <https://www.alfa.com/en/catalog/036218/> on May 17, 2022.
Google dated search results for "maltodextrin 12de" May 17, 2022.
Google dated search results for "alpha d lactose monohydrate pharmaceutical" May 17, 2022.
Glucidex Maltodextrin 12 product page (2015). Retrieved from <https://www.ulprospector.com/en/eu/Food/Detail/4917/363646/GLUCIDEX-MALTODEXTRIN-12> on May 17, 2022.
International Search Report and Written Opinion for PCT/GB2022/052983, mailed Jan. 20, 2023.
Office Action in U.S. Appl. No. 18/323,101, mailed Sep. 11, 2023.
Office Action in U.S. Appl. No. 18/323,115 (Nov. 22, 2023).
Office Action in U.S. Appl. No. 18/323,101 (Dec. 15, 2023).
International Search Report and Written Opinion for PCT/GB2022/052996, mailed Jan. 20, 2023.

* cited by examiner

PHARMACEUTICAL DEVICE FOR USE IN INTRANASAL ADMINISTRATION

This application is a continuation of International Application No. PCT/GB2022/052983, filed Nov. 25, 2022, which is hereby incorporated by reference in its entirety, and which claims priority benefit to Great Britain Application No. 2117016.2, filed Nov. 25, 2021.

This invention relates to new pharmaceutical devices and to methods of their manufacture.

PRIOR ART AND BACKGROUND

The listing or discussion of an apparently prior-published document in this specification should not necessarily be taken as an acknowledgement that the document is part of the state of the art or common general knowledge.

In the treatment of acute disorders a rapid onset of pharmacological effect than may be provided by peroral drug delivery is often highly desirable. Administration principles in which drugs are available immediately within systemic circulation are more likely to lead to a rapid onset of action.

Adrenaline, also known as epinephrine, is an endogenous hormone that is secreted mainly by the medulla of the adrenal glands, but also by a small number of neurons. Its primary role in the body is as a stimulator of components of the sympathetic nervous system. Adrenaline is typically released during stressful situations, and plays an important role in the fight-or-flight response by increasing blood flow to muscles, cardiac output, pupil dilation and plasma glucose levels. It exerts this effect by binding to, and stimulating, alpha and beta adrenergic receptors.

Adrenaline was first isolated in the late Nineteenth Century and is now commonly used exogenously as a medication, for example to treat allergic reactions (including anaphylaxis) and cardiac arrest, as well as croup and asthma.

For the treatment of severe and/or acute conditions, such as allergic reactions, including severe allergic reactions, anaphylaxis and anaphylactic shock (which may be caused by insect venom from stings or bites, certain foodstuffs or medications, and other chemicals, like latex), and in particular the emergency treatment thereof, adrenaline is presently administered parenterally by injection, for example subcutaneously, intravenously or intramuscularly, alongside other emergency medical interventions.

Those susceptible to such severe allergic reactions typically carry around an adrenaline autoinjector, which is self-administered in emergency situations. An autoinjector is typically a single-use, disposable, spring-loaded syringe, that is intended for self-administration by patients, or administration by untrained personnel or first responders, The most common adrenaline autoinjector device is sold under the brand name EpiPen® and EpiPen® Jr, but also under other brand names, such as Adrenaclick® and Auvi-Q®.

Injectable delivery means are often regarded as inconvenient. It is sometimes very difficult, if not impossible, for patients to self-administer drugs through needles, which sometimes necessitates wasteful and time-consuming intervention by first responders and/or physicians to ensure compliance, and to avoid effects that are either unwanted or detrimental.

Furthermore, all of the above-mentioned autoinjectors comprise solutions of adrenaline, which are extremely unstable chemically. Indeed, the EpiPen product label dictates that the product should be stored in its original packaging at room temperature (particularly between 20° C. and 25° C.) and kept away from light and moisture. It cannot be refrigerated or frozen (with a view to e.g. enhancing product stability), as this would be of detriment to the performance of the device in an emergency situation (given that it is necessary to inject a liquid solution through a fine needle).

Even under its prescribed storage conditions, the EpiPen has a shelf-life of a maximum of only 24 months, and the Epipen Jr a shelf-life of just up to 19 months. Furthermore, because of storage times during distribution, this shelf-life is often reduced by as much as 12 months by the time an end user is prescribed, or obtains, his or her device. The user is instructed in the product label to replace the unit before its expiry date.

Because of the instability of the adrenaline solution, in common of all autoinjectors, the EpiPen also comprises an inspection window, through which the user is instructed in the product label to inspect the product, in particular to check it visually for particulates (precipitation) or discoloration. If such particles and/or discoloration are present, the user is instructed to replace the unit, even if this occurs before the expiry date.

These factors conspire to increase the number of adrenaline autoinjectors that are wastefully disposed of, having not been used, but, in addition, adrenaline solutions tend to comprise stabilising agents (antioxidants), more particularly, sulfites, which many patients are allergic to, further limiting their use (see, for example, Roth and Shields, *Anesthesia & Analgesia*, 98, 1499 (2004)).

Thus, for the foregoing reasons, there is a significant unmet clinical need for a drug delivery composition comprising adrenaline that has improved stability (physically and, more importantly, chemically).

Transmucosal administration of active ingredients is a viable alternative to parenteral administration. It gives rise to the possibility of delivering drug molecules directly into systemic circulation through mucosal membranes (e.g. rectally, sublingually, buccally, pulmonarily and intranasally), and may lead to advantages, such as increased patient compliance, improved drug bioavailability and therefore lower doses, a more rapid onset of action and reduced side effects.

However, transmucosal administration of drugs presents its own, quite distinct problems. Unlike the gastrointestinal tract, which is a large organ that contains a relatively large amount of biological fluids, spaces such as the oral and nasal cavities are relatively small and contain much lower amounts of bodily fluids, such as saliva and/or mucous. This inevitably provides a considerable limitation on the amount of active ingredient that can be administered in a single dose.

Furthermore, although it is a dynamic system, the gastrointestinal tract is, in the main part, something of a 'closed' system. Conversely, the rapid clearance mechanisms that take place in both the oral and nasal cavities means that the time that is often available for absorption across a mucosal surface, for an already more limited amount of drug, is also limited.

Numerous formulation principles have been put forward to solve this problem, including, for example, bioadhesive formulation principles, such as buccal patches for oromucosal drug delivery (see, for example, Shojaei, *J. Pharm. Pharmaceutical Sci.*, 15, 19 (1998) and Gandhi, *Advanced Drug Delivery Reviews*, 43, 67 (1994)), as well as in situ gelling compositions for intranasal drug delivery (see, for example, Bertan et al, *Eur. J. Pharm. Sci.*, 27, 62 (2006)).

Transmucosal drug delivery systems that are in the solid state may present a significant advantage in allowing for higher drug loadings in the formulation. However, although solid drug delivery compositions are far more common when administering to rectal, buccal, sublingual and pulmonary mucosae, it remains the case that the vast majority of intranasal drug delivery systems are presented in the form of liquid sprays, typically aqueous solutions, wherein drug solubility plays yet another limiting factor in the amount of drug that is available for absorption.

That liquid sprays for intranasal delivery are almost ubiquitous is because formulating solid pharmaceutical formulations in form of a nasal powder is not easy. Unlike powders that are frequently employed for inhalation of active ingredients into the lungs, there are very few commercially-available intranasal powder formulations.

When formulated as dry powders, pulmonary drug delivery compositions typically take the form of 'aggregate' mixtures that include micronized particles of API on larger carrier particles. These aggregates are intended to dissociate/break up upon inhalation or actuation of a device, depositing only the fine particles of active ingredients in the lung.

However, such drug delivery systems are understood not to work effectively in the case of intranasal drug delivery. This is because the presence of such fine particles leads to a significant risk of lung exposure, which is not the intended site of administration. If drug particle sizes were increased to avoid this problem, it would likely lead to difficulties in ensuring appropriate interactions in the heterogeneous 'interactive' mixture, which depends on substantial differences in sizes of the two components to ensure interaction, in turn leading to potential manufacturing issues, such as segregation during filling. Attempting to compensate for this by correspondingly increasing carrier particle size would not necessarily solve the problem, but would necessarily increase the mass of inactive excipients in an already finitely limited total mass of dosage form, potentially resulting in a reduction in the dose of active ingredient.

The difficulties of formulating dry powders for intranasal delivery are dealt with in US Patent Application US 2005/001411 A1. In this document, it is stated that powders for nasal administration need to be fine enough so that they can be efficiently conveyed by a flow of gas and efficiently deposited in the nose, yet also coarse enough to facilitate the introduction of the powder into an appropriate powder device, which is always needed for intranasal administration. US 2005/001411 A1 apparently solves this problem by making loosely formed secondary particles (aggregates) of primary particles comprising active ingredients. The aggregates have dimensions that are a few hundreds of microns, and this is said to enable more efficient loading into an appropriate intranasal administration (an applicator, dispenser or insufflator) device. Upon actuation of such a device, and administration of the composition, the aggregates apparently quickly break up into the primary particles of active ingredients. These primary particles are of a size that is just a few microns, which is stated to facilitate their dissolution and, thereafter, intranasal absorption of active ingredient.

As stated above, transmucosal (e.g. intranasal) delivery of drugs intended for systemic absorption avoids the first pass metabolism that is inevitably a component of peroral administration. Drug metabolism occurs through chemical reactions with enzymes that are capable of altering an active ingredient's chemical structure, physical structure and/or biological activity.

Because most drugs are organic molecules that contain functional groups that are capable of undergoing such chemical reactions, they are often susceptible to some form of chemical decomposition when they come into contact with substances that are capable of interacting with those functional groups outside of the body. As discussed above, chemical instability problems are particularly acute in the case of adrenaline.

As is summarised by Kou and Zhou in Chapter 16 of the textbook *Amorphous Solid Dispersions*, Shah et al (Eds.), Springer (2014), if a drug is formulated in an amorphous, as opposed to a crystalline, physical state, it is typically presented in a higher energy state, and is thus likely to be more chemically and physically unstable, presenting challenges to pharmaceutical formulators.

Chemical stability is thus often improved by presenting a drug in a crystalline state, often through salt formation. The primary objective of salt formation is usually to increase hydrophilicity of active ingredients in order to address poor aqueous solubility and dissolution rate issues. However, in making a salt, other physicochemical and biological concerns, such as chemical stability, can often be simultaneously addressed. For example, basic drugs (e.g. drugs containing at least one amine group) are often presented in the form of an acid addition salt, which salts are typically more stable chemically than the corresponding 'free' amine bases.

However, whilst potentially providing active ingredient in a form in which it can be more easily stored without chemical degradation, and more efficient in terms of its rate and/or extent of dissolution after administration, crystalline salts generally have slower dissolution rates and are less efficiently absorbed across mucosal membranes, than if corresponding active ingredients are presented in an amorphous, and/or unionized form, respectively.

Thus, active pharmaceutical ingredients formulated as amorphous solid dispersions generally have the advantage of higher bioavailability, but typically present challenges in the form of reduced physical and chemical stability, whereas drugs formulated in a crystalline and/or salt form, whilst generally being more stable tend to be less bioavailable.

The latter problem can be particularly disadvantageous in the case of transmucosal, such as intranasal or sublingual, drug delivery, where, as discussed above, residence times of drugs in the relevant cavity, within which absorption into systemic circulation needs to occur, is limited. This, coupled with poor permeability across mucous membranes at physiological pHs may lead to unacceptably low and/or slow transmucosal absorption to provide for an adequate therapeutic effect.

Many elaborate formulation principles have been devised over the years to address the balancing act between solubility and permeability in transmucosal drug delivery systems. Such formulation principles include the addition of pH modifying substances that convert an ionized salt form of active ingredient into a more permeable unionized state.

However, in view of all of the aforementioned potential advantages that it offers, there remains a general need for improved solid (e.g. powder-based) transmucosal and especially intranasal drug delivery systems.

In particular, there remains a significant unmet clinical need in the field of transmucosal drug delivery, for a powdered drug delivery composition that:
  (i) is both physically and chemically stable; and
  (ii) provides active ingredient:
     at a sufficient dose; and/or
     in a form in which it is permeable enough
  to provide a required therapeutic effect (such as speed of onset and/or access to a drug target) at the (relatively speaking) low doses that are possible, and short residence times that are available, in the transmucosal context, such as within the nasal cavity.

In the more specific field of intranasal drug delivery, there remains a significant unmet clinical need for such a drug delivery composition that comprises particles of an appropriate size to enable both the efficient:

filling of a drug delivery device; and
deposition within the relevant (e.g. nasal) cavity.

Intranasal dry powder formulations are known from inter alia international patent applications WO 2010/142696 and WO 2019/038756, U.S. Pat. No. 10,653,690 B2 and US patent application US 2018/0092839A. See also U.S. Pat. Nos. 7,947,742 B2, 8,415,397 B2 and 8,747,813 B2.

Russo et al (*J. Pharm. Sci.*, 95, 2253 (2006)) discloses spray-drying the opioid analgesic compound, morphine, with numerous excipients. Spray-dried formulations are also disclosed in Vengerovich et al., *Bulletin of Experimental Biology and Medicine,* 163, 737 (2017), where it was attempted to microencapsulate an active ingredient in various substances, including 2-hydroxypropyl-β-cyclodextrin, with a view to developing sustained-release preparations based on polymeric carriers for emergency care.

We have now found that it is possible to formulate an adrenergic receptor modulator, such as adrenaline, in the form of amorphous dry powder compositions by way of a process that, for example, spray-dries that active ingredient along with a carrier material, as disclosed hereinafter. When loaded into applicator devices, astonishing improvements in stability of those active ingredients, during storage and prior to administration is observed, when compared to currently-available devices such as the EpiPen. Such compositions may in addition provide for improved bioavailability and/or speed of absorption of such active ingredients following administration

DISCLOSURE OF THE INVENTION

Figures 1, 2:
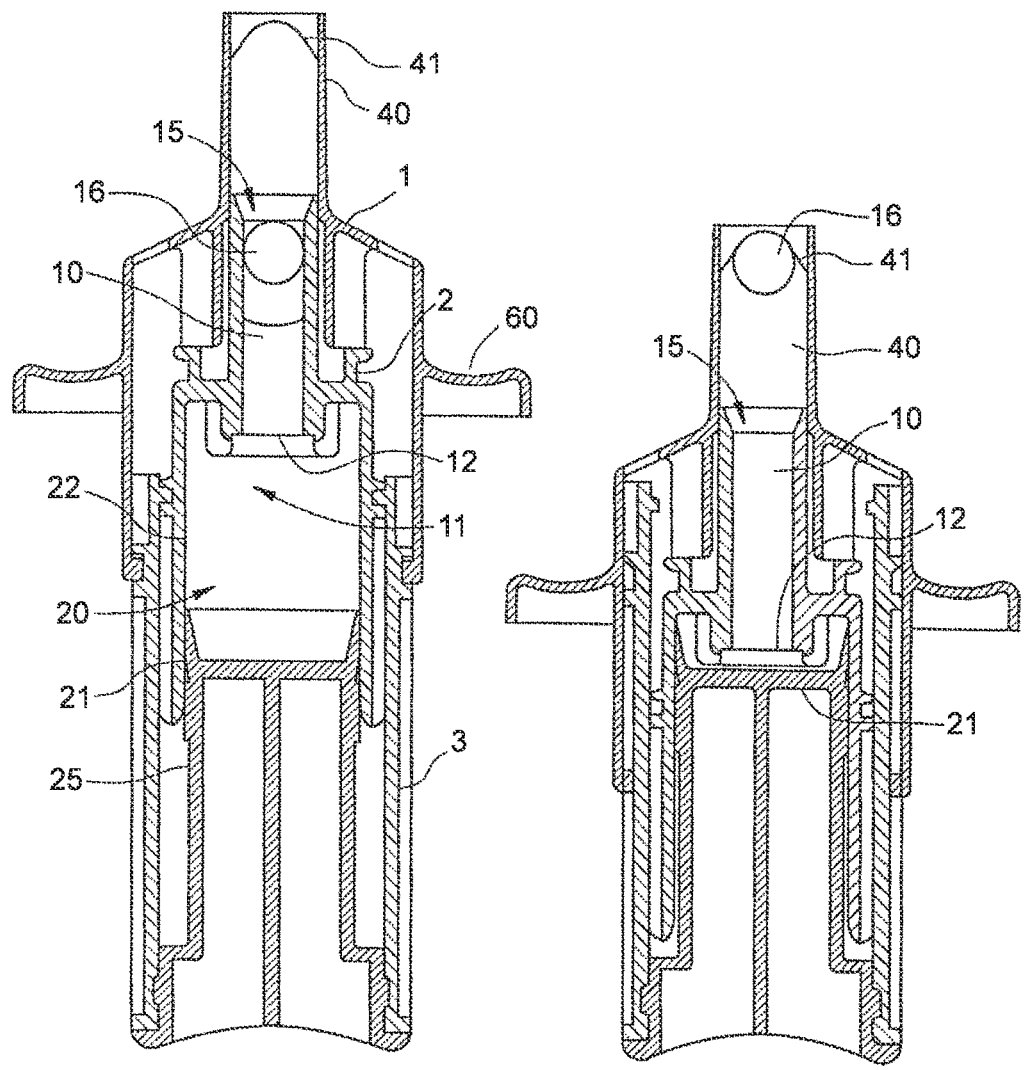
FIGS. 1 to 7 represent drawings of actuator devices that may be used to dispense compositions of the invention.
Figure 3:
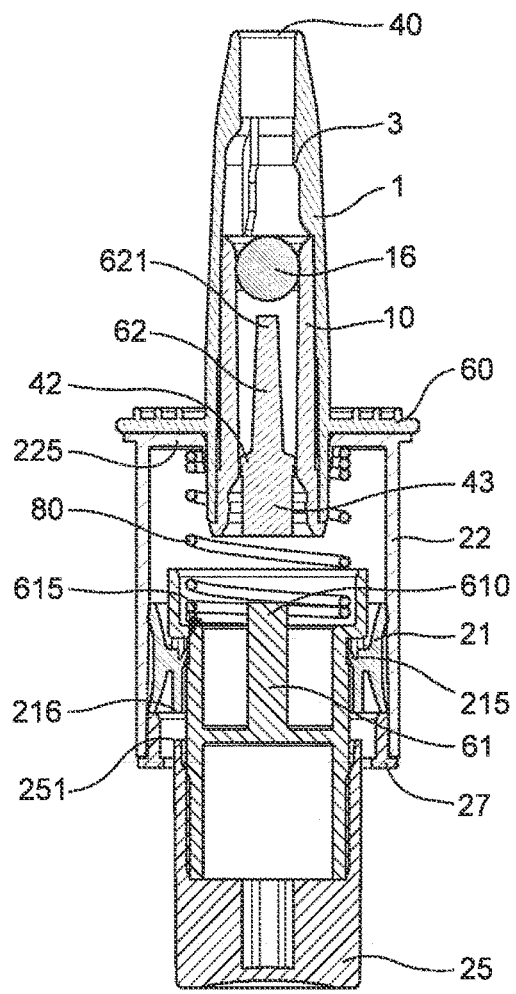

According to a first aspect of the invention, there is provided a needle-free applicator that is suitable for administering a solid, amorphous, mono-particulate powder into a body cavity of a human patient, which cavity includes a mucosal surface, wherein the applicator comprises:
(i) an opaque reservoir comprising said solid, amorphous, mono-particulate powder composition;
(ii) an optional actuating means for generating a force upon actuation of the device by a user; and
(iii) a dispensing means through which, following said actuation, said powder composition may be dispensed,
wherein said solid, amorphous, mono-particulate powder composition comprises a pharmacologically-effective dosage amount of an adrenergic receptor modulator, or a pharmaceutically-acceptable salt thereof, encapsulated in an amorphous state along with a pharmaceutically-acceptable carrier material; and which powder composition is less than about 4% chemically degraded after storage for:
(a) at least about 3 months at 40° C. and 75% relative humidity;
(b) at least about 18 months at below about 30° C.; and/or
(c) at least about 18 hours at above about 1 million lux of UV light.

The term 'needle-free' means an apparatus for administering an active pharmaceutical ingredient that does not comprise an injection means that further includes a means of puncturing e.g. the skin or a mucosal surface, in order to inject said active ingredient into the body, for example subcutaneously or intramuscularly (as the aforementioned adrenaline autoinjectors do). Such needle-free applicators, as defined above, are referred to hereinafter together as 'the applicators of the invention'.

Modulators (also known as 'stimulators' or 'agonists') of adrenergic receptors (including the $\alpha_{1A}$, $\alpha_{1b}$, $\alpha_{1c}$, $\alpha_{1d}$, $\alpha_{2a}$, $\alpha_{2b}$, $\alpha_{2c}$, $\alpha_{2d}$, $\beta_1$, $\beta_2$, $\beta_3$ sub-receptors) that may be mentioned may include phenylephrine, oxymetazoline, methyldopa, clonidine, dexmedetomidine, lofexidine, dobutamine, mirabegron, dopamine, albuterol (salbutamol), formoterol, levalbuterol, olodaterol, salmeterol, pirbuterol, terbutaline, fenoterol, rimiterol, hexoprenaline, tretoquinol, karbuterol, tulobuterol, clenbuterol, procaterol, bitolterol, indacaterol, colterol, pseudoephedrine, ephedrine, more preferably norepinephrine, isoprenaline and, particularly, epinephrine (referred to hereinafter as 'adrenaline' for the sake of consistency).

Compositions that are included, and/or are for inclusion, in a reservoir of an applicator of the invention are in the form of an amorphous, mono-particulate powder. By 'mono-particulate', we mean that the plurality of particles that form those powdered compositions comprise a homogeneous or a heterogeneous mixture, in which an adrenergic receptor modulator or salt thereof is encapsulated in an amorphous state within the carrier material as defined above, optionally in the presence of other ingredients. The particles of the powdered compositions for inclusion in the reservoir of the applicator of the invention are thus presented as an amorphous composite of the adrenergic receptor modulator or pharmaceutically-acceptable salt thereof (hereinafter referred to as 'active ingredient'), the carrier material and, optionally, other ingredients.

By being amorphous in their nature, such powder compositions may be wholly amorphous and/or may be predominantly amorphous (for example more than about 50% by weight, such as more than about 75% by weight, including more than about 80% by weight, such as more than about 90% by weight, or 95% by weight, including more than about 99% by weight amorphous). In the alternative, powder compositions may be less than about 50%, such as less than about 25%, more preferably less than about 20%, for example less than about 10%, including less than about 5%, or less than about 1% crystalline. The degree (%) of crystallinity may be determined by the skilled person using powder X-ray diffraction (PXRD). Other techniques, such as solid-state NMR, FT-IR, Raman spectroscopy, differential scanning calorimetry (DSC) microcalorimetry, and calculations of true density, may also be used.

As described hereinafter, despite being in an amorphous physical state, compositions that may be included in the reservoir of the applicator of the invention exhibit remarkable and unexpected physical and chemical stability, and may thus be provided in the form of pharmaceutical products that show excellent shelf-life when stored under normal storage conditions.

The stability of the powder compositions described herein is excellent, both prior to the loading into the reservoir of an applicator of the invention, and also once said powder compositions have been loaded into the reservoir. In the latter situation, stability is preserved (if not improved). In any event, compositions that may be included in applicators of the invention may be stored, either within such applicators or as bulk powders under the conditions described herein without significant chemical degradation.

Compositions that may be employed in applicators of the invention are provided as powders (i.e. in multiparticulate form) by an appropriate technique. In general, appropriate techniques fall into 'solvent-based' methods, which include spray-drying, fluidized bed techniques, co-precipitation, supercritical fluid techniques, spray granulation, cryogenic techniques (including freeze-drying), electrospinning and rotating jet techniques, or 'fusion-based' methods, which include melt granulation, melt extrusion, high-shear mixing (e.g. KinetiSol®), milling and molten material on carrier techniques (e.g. Meltdose®). Preferred methods include freeze-drying and, more preferably, compositions to be employed in applicators of the invention are made by a process of spray drying.

Compositions for inclusion in a reservoir of an applicator of the invention may be provided in any multi-particulate form (e.g. as simple powders, granules, pellets and/or beads), comprising a plurality of particles that may individually and/or may collectively consist essentially of, and/or comprise, one or more such composition(s).

Said compositions may thus be presented following their preparation (e.g. by spray-drying) in the form of simple powder mixtures, powder microspheres, coated powder microspheres, a lyophilised liposomal dispersion, or a combination thereof.

If a powder composition for inclusion in an applicator of the invention 'consists essentially of' those particles, this will be understood to mean that that reservoir of the applicator comprises only one or more such compositions, along with other features and/or components that do not materially affect the basic and novel characteristic(s) of the applicator of the invention, or the composition contained therein. Alternatively, in situations where the applicators of the invention 'consist essentially of' one or more powder compositions as defined herein, this may be understood to mean that that the applicator of the invention comprises at least about 90%, such as at least about 95%, including at least about 97% (e.g. about 99%) by weight of those one or more of such composition(s) in total. Applicators of the invention may, in the alternative, comprise more than one such composition(s).

Appropriate techniques for making multiparticulates comprising dry powders or granulates include simple dry mixing, granulation (including dry granulation, wet granulation, melt granulation, thermoplastic pelletising, spray granulation), extrusion/spheronisation or more preferably, freeze-drying or spray-drying (vide infra).

Dry granulation techniques are also well known to those skilled in the art and include any technique in which primary powder particles are aggregated under high pressure, including slugging and roller compaction, for example as described hereinafter.

Wet granulation techniques are well known to those skilled in the art and include any technique involving the massing of a mix of dry primary powder particles using a granulating fluid, which fluid comprises a volatile, inert solvent, such as water, ethanol or isopropanol, either alone or in combination, and optionally in the presence of a binder or binding agent. The technique may involve forcing a wet mass through a sieve to produce wet granules which are then dried, preferably to a loss on drying of less than about 3% by weight.

Melt granulation will be known by those skilled in the art to include any technique in which granules are obtained through the addition of a molten binder, or a solid binder which melts during the process (which binder materials may comprise the pharmaceutically acceptable carrier materials of the composition that is to be used in an applicator of the invention). After granulation, the binder solidifies at room temperature. Thermoplastic pelletising will be known to be similar to melt granulation, but in which plastic properties of the binder are employed. In both processes, the agglomerates (granules) obtained comprise a matrix structure.

Extrusion/spheronisation will be well known to those skilled in the art to include any process involving the dry mixing of ingredients, wet massing along with a binder, extruding, spheronising the extrudate into spheroids of uniform size, and drying.

Spray granulation will be known by those skilled in the art to include any technique involving the drying of liquids (solutions, suspensions, melts) while simultaneously building up granulates in a fluid bed. The term thus includes processes in which foreign seeds (germs) are provided upon which granules are built up, as well as those in which inherent seeds (germs) form in the fluid bed due to abrasion and/or fracture, in addition to any spray coating granulation technique generally. The sprayed liquid coats the germs and assists further agglomeration of particles. It is then dried to form granules in the form of a matrix.

The term 'freeze drying' includes lyophilisation or cryodesiccation, and any low temperature desolvatization (e.g. dehydration) process, in which product is frozen, pressure is lowered, and the frozen solvent (e.g. water) is removed by sublimation.

As described herein, compositions that may be employed in applicators of the invention are preferably made by a process of spray-drying.

Compositions for inclusion in applicators of the invention may otherwise be prepared by standard techniques, and using standard equipment, known to the skilled person. In this respect, the compositions for inclusion in a reservoir of an applicator of the invention may be combined with conventional pharmaceutical additives and/or excipients used in the art for relevant preparations, and incorporated into various kinds of pharmaceutical preparations using standard techniques in order to make applicators of the invention (see, for example, Lachman et al, *'The Theory and Practice of Industrial Pharmacy'*, CBS, $4^{th}$ edition (2015); *'Remington: The Science and Practice of Pharmacy'*, Troy (ed.), Elsevier, $23^{rd}$ edition (2020); and/or *'Aulton's Pharmaceutics: The Design and Manufacture of Medicines'*, Taylor and Aulton (eds.), Elsevier, $5^{th}$ edition, 2017).

However, they are manufactured, it is preferred that compositions that are included in applicators of the invention are suitable for, and/or are formulated for, transmucosal delivery of the active ingredient into systemic circulation.

The term 'transmucosal' will be understood by those skilled in the art to mean that, however it is administered to a patient, a composition is presented at a relevant mucosal surface in such a form that the active ingredient(s) may be absorbed across that mucosal surface following its dissolution. Relevant mucosal surfaces thus include the oral, nasal, ocular, vaginal, cervical, pulmonary and/or anorectal mucosae, more particularly the oral mucosa (including buccal and sublingual mucosae) and the nasal mucosa.

In this respect, applicators of the invention may be used to deliver the powder composition that is contained therein directly to a body cavity of a patient that comprises a mucosal surface (including pulmonarily, rectally, vaginally, buccally, sublingually or intranasally), for transmucosal delivery of active ingredient.

Thus, such compositions may be administered sublingually by discharging the powder composition as described herein into the mouth and under the tongue from an applicator of the invention.

If compositions for inclusion in a reservoir of an applicator of the invention are suitable for, and/or are formulated for sublingual or, more notably, intranasal administration, then they are preferably administered in the form of a powder in which the dosage amount of the active ingredient is no more than about 100 mg. Such sublingual and/or nasal powder compositions may comprise a composition for inclusion in a reservoir of an applicator of the invention as defined herein admixed with other excipients, or may consist essentially of said composition as hereinbefore defined.

Applicators of the invention that are suitable for intranasal administration may contain one spray-dried powder composition within a reservoir of said applicator, or may contain two or more such compositions. In the latter instance, the applicator may contain two or more dosing amounts of said powder composition, which dosing amounts will each contain a pharmacologically-effective dose of the active ingredient(s).

Two or more such compositions may be administered intranasally by repeated actuation of an appropriate applicator of the invention. Appropriate devices (e.g. nasal applicators or dispensers (insufflators) are described hereinafter. Compositions for inclusion in a reservoir of an applicator of the invention may be presented within such a reservoir that is part of, is adjunct to, and/or is suitable for being placed adjunct to, an applicator to form an applicator of the invention. Such a container or reservoir may contain the one or more powder compositions, each containing a pharmacologically-effective dosage amount of active ingredient.

In this way, appropriate dosing means and/or nasal applicators may be actuated only once to deliver a single powder composition comprising an appropriate dose of an active ingredient following that actuation (i.e. a single-use dosing unit), may be actuated more than once to deliver two or more such powder compositions, each comprising an appropriate dose of the active ingredient, upon each such actuation (i.e. a multiple-use dosing unit), and/or applicators may be re-filled with a replacement source of said composition (e.g. a container or reservoir), comprising one or more such powder compositions, to provide for single and/or multiple doses and/or dosing regimens.

Compositions that are included in an applicator of the invention are thus administered in the form of a plurality of particles, which particles may individually and/or collectively consist of, and/or comprise, a powder composition as defined herein.

Such compositions are prepared in the form of solid, dry, free-flowing, multi-particulate powders.

By 'dry' we include essentially free of water and other liquid solvents, which includes that there is less than about 10%, such as less than about 6%, including less than about 5%, or less than about 4%, more preferably less than about 3%, such as less than about 2%, e.g. less than about 1% of the formulation is a liquid, such as water.

The term 'solid' will be well understood by those skilled in the art to include any form of matter that retains its shape and density when not confined, and/or in which molecules are generally compressed as tightly as the repulsive forces among them will allow. An essentially solid composition is thus one that is at least about 80%, such as at least about 90%, including at least about 95% (or at least about 99%) in such a form.

Flowability of powder compositions of the invention may be measured by standard techniques known to those skilled in the art including bulk density measurements, or measurements taken on a powder flow analyser (for example those sold by Stable Micro Systems or Meritics, both UK), including powder flow speed dependence tests, caking tests, cohesion tests, etc. A preferred measurement of flowability is the standard angle of repose, which may be carried out using a revolving cylinder, a fixed funnel or a tilting box.

In the context of the present invention, the term 'free-flowing' is intended to include a powder that allows for efficient filling of a composition into an applicator of the invention (i.e. a drug delivery device) during manufacturing, and/or provides a sufficient shot weight when expelled from the device (vide infra).

The term may also include that the powder exhibits an angle of repose of no more than about 50°, such as no more than about 45°, including no more than about 40°, for example no more than about 35°, and more particularly no more than about 30°; a bulk density of no less than about 0.3 g/mL, for example no less than about 0.4 g/mL, such as no less than about 0.5 g/mL, and more particularly no less than about 0.6 g/mL; and/or a tap density of no less than about 0.5 g/mL, such as no less than about 0.6 g/mL, for example no less than about 0.7 g/mL, and in particular no less than about 0.8 g/mL.

Being in the form of amorphous, mono-particulate powders, compositions for inclusion in applicators of the invention are not composed of physical associations of two or more discrete, separate sets of particles of different ingredients in the form of a mixture, such as an ordered, or interactive, mixture of smaller particles of active ingredient associated with larger, but separate and chemically distinct, particles of carrier substances. That said, powder compositions as described herein may be provided as small particles which may subsequently be adhered to separate, larger carrier particles in an interactive mixture, and such a presentation may be useful if the dosage form that is intended for inhalation, for example to the lung, (see e.g. *J. Drug Delivery*, Art. ID 5635010, 1-19 (2018)).

As mentioned hereinbefore, the process of making compositions for inclusion in applicators of the invention enables the formation of pharmaceutical products that show excellent shelf-life, in terms of both physical and chemical stability, when stored under normal storage conditions, as defined herein.

Compositions for inclusion in applicators of the invention are preferably prepared by a process of spray-drying. The process of 'spray-drying' will be understood by the skilled person to include any method of producing a dry powder from a liquid, including a solution or a suspension (including a slurry) that involves rapid drying using hot gas to convert a stream of liquid into vaporized solvent and particles of solid, which solid particles comprise the solute that was previously dissolved in a solution, and/or particles that were previously suspended in the evaporated liquid.

Appropriate spray-drying equipment includes some form of atomization means, such as a spray nozzle, which disperses the liquid into a spray with a relatively uniform droplet size. Such means may include any means that is capable of producing a dry, free-flowing powder, and may include high pressure swirl nozzles, rotary disks and/or atomizer wheels, high pressure single fluid nozzles, two-fluid nozzles and/or ultrasonic nozzles.

The spray-dryer may be a single effect or a multiple effect spray-dryer, and may comprise an integrated and/or an external vibrating fluidized bed, a particle separator, and/or a collection means which may be a drum or a cyclone.

According to a further aspect of the invention, there is provided a process for the manufacturing of an applicator of the invention, wherein said process comprises the steps of:
i) mixing together the adrenergic receptor modulator or pharmaceutically-acceptable salt thereof, and the pharmaceutically-acceptable carrier material, in an appropriate volatile solvent,
ii) spray-drying the mixture from step i),
iii) loading the product from step ii) into a reservoir of an applicator of the invention.

Preferred volatile solvents include water, or organic solvents, such as lower alkyl alcohols (e.g. methanol, isopropanol or, more especially, ethanol), hydrocarbons (e.g. $C_{5-10}$ alkanes), haloalkanes (e.g. dichloromethane), dimethylformamide, dimethylsulfoxide, ethyl acetate, acetone, etc., or mixtures thereof.

We prefer that mixing together the one or more active ingredients, pharmaceutically-acceptable carrier material(s) as defined herein, and other optional ingredients as described herein (for example alkyl saccharides as described hereinafter), with the solvent results in a solution that can be spray-dried.

The pharmaceutically-acceptable carrier material that is employed in a composition for inclusion in an applicator of the invention should be suitable (and/or approved) for pharmaceutical use and/or for transmucosal (e.g. sublingual or, notably, intranasal) delivery, capable of maintaining its physical and/or chemical integrity, and/or not affect the physical and/or chemical integrity of the active ingredient and/or any other ingredients that are or may be present in the composition (such as alkyl saccharide), in the solid state, under normal storage conditions.

It is well known that significant difficulties may be experienced in attempting to obtain both chemically- and physically-stable solid compositions, such as powders. If the physical form of a composition changes under normal storage conditions (e.g. from a free-flowing powder to an agglomerated mass that is difficult to discharge), it will likely lead to non-reproducibility of dose of active ingredient. This is particularly so when dispensing a composition from, or via, a nasal applicator as described herein, where such agglomeration may result in the complete inability to dispense the active ingredient, which could be catastrophic in an emergency situation.

Compositions that are included in applicators of the invention may this have a minimum shot weight, as measured by individual powder shot weight relative to target weight of about 80%, such as about 85% (e.g. about 90%) up to about 120% (e.g. about 115%, such as about 110%), and/or a mean powder shot weight relative to target weight of about 85%, such as about 90% (e.g. about 95%) up to about 115% (e.g. about 110%, such as about 105%).

Similarly, for multiple dose units containing two or more doses of a composition, such stability is critical to ensure reproducibility of the dose of active ingredient over time. Either of these problems may have a detrimental effect on a subject's health, and/or put a subject's well-being at significant risk.

For certain compositions that are to be included in an applicator of the invention, exposure to atmospheric water may result in powder compositions that are less solid-state stable. For example, exposure to certain (e.g. higher) relative humidities may affect the physical form of the composition, for example by deliquescence, and/or by lowering glass transition temperatures of compositions, and/or individual components of the compositions, such as carrier materials, or in another way.

Accordingly, compositions for inclusion in reservoirs of the applicators of the invention, and applicators of the invention including them, are preferably packaged within containers that substantially prevent the ingress of atmospheric water under the storage conditions defined herein. Such containers may include packaging materials, such as blister packs and heat-sealed aluminium pouches and/or thermoformed plastics. Such containers may also comprise a desiccant, such as silica gel and/or appropriate molecular sieves, with a pore size of e.g. 3 Å or 4 Å.

The phrase 'maintaining physical and chemical integrity' essentially means chemical stability and solid-state stability.

By 'chemical stability', we include that any powder composition described herein may be stored in isolated solid form, when formulated into an applicator of the invention or a reservoir therefor (with or without appropriate pharmaceutical packaging) or otherwise, under normal storage conditions, with an insignificant degree of chemical degradation or decomposition of either the composition per se or the active ingredient included therein.

The term 'chemical stability' also includes 'stereochemical' and/or 'configurational' stability, by which we mean resistance to stereochemical conversion, such as racemisation, at one or more chiral centres within a molecule of an active ingredient. This is particularly important in the case of adrenaline, where the R-enantiomer (i.e. the L-(−)-epinephrine) is the active enantiomer, and the S-enantiomer (i.e. the D-(+)-epinephrine) is less active and may therefore be considered to be an impurity.

By 'physical stability', or 'solid-state stability', we include that any powder composition described herein may be stored in an isolated solid form, when formulated into an applicator of the invention or a reservoir therefor (with or without appropriate pharmaceutical packaging) or otherwise, under normal storage conditions, with an insignificant degree of solid-state transformation (e.g. crystallisation, recrystallisation, loss of crystallinity, solid-state phase transition (e.g. between a glassy or a rubbery state, or to an agglomerated form)), hydration, dehydration, solvatisation or desolvatisation of either the composition per se or the active ingredient included therein.

Examples of 'normal storage conditions' for applicators of the invention include temperatures of between about −50° C. and about +80° C. (preferably between about −25° C. and about +75° C., such as about 50° C.), and/or pressures of between about 0.1 and about 2 bars (preferably atmospheric pressure), and/or exposure to at least about 460 lux of UV/visible light, and/or relative humidities of between about 5 and about 95% (preferably about 10 to about 40%), for prolonged periods (i.e. greater than or equal to about twelve, such as about six months).

Under such conditions, compositions that are included in applicators of the invention (and/or active ingredients contained therein) may be found to be less than about 15%, more preferably less than about 10%, and especially less than about 5%, chemically degraded/decomposed, and/or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

Such chemical and, particularly, physical stability is of importance in a solid-state composition, such as a powder, to ensure that the appropriate dose is delivered to the patient.

Notwithstanding the above definition of 'normal storage conditions', powder compositions (and/or active ingredients contained therein) for inclusion in reservoirs of applicators of the invention are less than about 5%, such as less than about 4% (including less than about 3%, such as less than about 2.5% (e.g. about 2%), including less than about 1.5% and even less than about 1%) chemically, and/or stereochemically, degraded after storage for:
  (a) at least about 3 months, including at least about 6 months or at least about 12 months, at 40° C. and 75% relative humidity;
  (b) at least about 18 months, such as at least about 24 months, including at least about 36 months at below about 30° C., such as about 30° C. or about 25° C. and/or at, for example, about 65%, such as about 60%, relative humidity; and/or
  (c) at least about 18 hours at above about 1 million lux of UV light.

Applicators of the invention can therefore be stored at any temperature (e.g. as low as about −20° C.) up to about 25° C. (e.g. up to about 30° C.), preferably with excursions up to about 40° C. or even up to about 50° C.

Particularly preferred pharmaceutically-acceptable carrier materials that may be employed to produce compositions for use in applicators of the invention, and which possess the desirable characteristics mentioned herein, include disaccharides and polymeric material components, especially if employed in combination.

Appropriate disaccharide components include maltitol, sucralose, sucrose, isomalt, maltose, preferably lactose (including β-D-lactose and α-D-lactose, especially α-D-lactose monohydrate) and more preferably trehalose.

Appropriate polymeric material components that may be employed as pharmaceutically-acceptable carrier materials in powder compositions for use in applicators of the invention, and which possess the desirable characteristics mentioned herein, include cellulose and its derivatives, such as sodium carboxymethyl cellulose, ethyl cellulose, cellulose acetate, hydroxypropylmethyl cellulose (hypromellose, HPMC), hydroxyethyl cellulose (HEC), hydroxypropyl cellulose (HPC), methyl cellulose (MC), ethyl hydroxyethyl cellulose, carboxymethyl cellulose (CMC), modified cellulose gum, microcrystalline cellulose and sodium carboxymethyl cellulose; starches, such as rice starch, tapioca starch, wheat starch and, more particularly, corn starch and potato starch; starch derivatives, such as pregelatinized starch, carboxymethyl starch, as well as moderately cross-linked starch, modified starch and sodium starch glycolate; polysaccharides, including dextran, pullulan, inulin and dextrins, such as dextrin, cyclodextrins and linear or branched dextrins, such as maltodextrins; powdered tragacanth; waxy excipients, such as cocoa butter and suppository waxes; polyols, such as solid polyethylene glycols; acrylic polymers, such as carbomer and its derivatives; polyvinylpyrrolidone (povidone, PVP); crosslinked polyvinylpyrrolidone; polyethylene oxide (PEO); chitosan (poly-(D-glucosamine)); natural polymers, such as gelatin, sodium alginate, pectin; scleroglucan; xanthan gum; guar gum; poly co-(methylvinyl ether/maleic anhydride); and croscarmellose (e.g. croscarmellose sodium). Hypromellose acetate succinate (HPMCAS), copovidone and polyvinyl alcohol (PVA, or PVOH) may also be mentioned.

More preferred polymeric materials include sodium carboxymethyl cellulose, sodium starch glycolate, polyvinylpyrrolidone and, particularly, hydroxypropylmethyl cellulose (such as hypromellose 2906, preferably hypromellose 2910 (i.e. 'E'-types), and more preferably USP/NF hypromellose 2208 (i.e. 'K'-types)), and the like, or, particularly, polysaccharides, such as dextrins, including cyclodextrins (e.g. α-, β- and γ-cyclodextrins and derivatives thereof, such as, 2-hydroxypropyl-γ-cyclodextrin, sulfobutylether β-cyclodextrin sodium salt, randomly methylated β-cyclodextrin, branched β-cyclodextrin and the like and, particularly, 2-hydroxypropyl-β-cyclodextrin); and linear or branched dextrins, such as maltodextrins.

In any event, suitable polymers for use in compositions that are employed in applicators of the invention should have a molecular weight that is high enough such that, when it is employed in any given amount, for example in combination with a disaccharide, it is capable of forming a suitable carrier material for the active ingredient.

For any given polymer, polymer chain length (and therefore molecular weight) is directly proportional to its viscosity. Put another way, the viscosity of a solution of that polymer is proportional to the molecular weight or chain length of the specific polymer.

In this respect, it may be preferred that the polymer has a relative viscosity value at 20° C. of no more than about 1000 (more preferably no more than about 120, such as no more than about 60, and particularly no more than about 10) mPa*s, as measured, for any given and essentially:
  (a) water-soluble polymer, as a 2 wt % solution of the polymer in water by the standard USP methods for viscosity, i.e. <911> Method I, and/or <912> Method I; and
  (b) water-insoluble polymer, as a 5 wt % solution of the polymer in a suitable organic solvent, such as acetone, methanol, ethanol, isopropyl alcohol, ethyl acetate, acetonitrile, dichloromethane, toluene and mixtures thereof, which solvent system may be dry or partly aqueous, by the USP method <911> Method I.

The skilled person will understand which test is more suitable for the polymer tested.

Amounts of carrier materials that may be employed in compositions for inclusion in applicators of the invention are typically in the range of about 5% to about 99.9%, including up to about 99% (e.g. up to about 95% or about 90%), such as about 10% (e.g. about 25%, including about 35%) to about 85%, including about 50% to about 75%, by weight, based upon the total weight of the composition (whether one dose of said composition is included in the applicator of the invention or otherwise).

Whether provided as a combination of materials or otherwise, it is preferred that the carrier material is capable of giving rise to a composition for inclusion in an applicator of the invention that possesses a glass transition temperature (Tg) that:
  (a) enables its production as a hard and/or brittle, 'glassy', amorphous, powdered physical form, that can be easily formulated into a pharmaceutical formulation or dosage form, and thereafter loaded into an applicator of the invention, such as a nasal applicator, or a drug reservoir and/or container within, or adjunct to, such an applicator, as described herein; and
  (b) is high enough that, after such an applicator or reservoir is packaged as described herein, and thereafter subjected to a high external temperature (e.g. up to between about 50° C. and about 80° C.), it remains in that glassy state, rather than being transformed into a more viscous or rubbery state, and/or a crystalline state.

Such extreme external temperatures are often experienced inside vehicles (e.g. of first responders) in warm and/or sunny climates, which vehicles will frequently be parked for extended periods of time in full sun, where the resultant heat gain can be enormous. If the Tg of a powder composition is low, the composition may transform after exposure to such high temperatures to such a viscous/rubbery state, this will give rise to inefficient dosing of the composition, for example inefficient discharging of the composition from an applicator of the invention or reservoir contained therein (and so too the dose(s) of active ingredient) once the applicator is actuated.

In this respect, we prefer that the lowest measurable Tg of a composition for inclusion in an applicator of the invention is at least about 35° C., including at least about 40° C., such as at least about 50° C., such as at least about 55° C., including at least about 60° C., when measured at a relative humidity of up to about 35%, such as up to about 30%, including up to about 25% (e.g. up to about 20%, such as less than about 15%, e.g. less than about 10%). By 'lowest measurable Tg', we include that the powder composition in question may comprise particles that are heterogenous in their nature. In particular, particles may comprise discrete regions of the carrier materials, or composite mixtures thereof, and so may possess individual and separate Tg values. It will be clear to the skilled person that the value of the lowest measurable Tg has a strong impact on the physical stability of the composition.

We have found that relative amounts of the disaccharide and the polymer ingredients in the carrier material (and particularly so when the polymer is a dextrin) can be tailored to ensure the required level of physical and/or chemical stability of active ingredient whilst, at the same time, not lowering the Tg of the composition for inclusion in applicators of the invention in such a manner that it affects its physical stability.

We have found that a ratio of between about 50:1 to about 1:50 of disaccharide:polymer (e.g. dextrin) by weight, based on the total weight of the composition, may work depending on the active ingredient that is employed. Preferred ratios are in the range of about 10:1 to about 1:40 (including up to about 1:30 or up to about 1:20), for example between about 7:1, including about 5:1, such as about 4:1, about 3:1 or about 2:1, and about 1:10, such as about 1:8, including about 1:5, for example 1:3 or 1:2, more preferably about 8:1 (e.g. about 7:1, about 3:1, about 2:1 or about 1:1) to about 1:8 (e.g. about 1:3 or about 1:2) of disaccharide:polymer (e.g. dextrin) by weight, based on the total weight of the composition.

A particularly preferred combination of carrier materials thus includes trehalose or a lactose, such as α-D-lactose monohydrate, and a dextrin, and especially a cyclodextrin, such as 2-hydroxypropyl-β-cyclodextrin, or, more preferably, a maltodextrin.

Maltodextrins are classified by DE (dextrose equivalent), with the higher the DE value, the shorter the average length of the glucose chains. Preferred maltodextrins include those with a DE of between 6 and 15, such as 8 and 12, or above 15, for example up to 47, such as 38, 39, preferably 23, 24, 25 or 26, or, more preferably, 16, 17, 18, 20, 21 or 22, and especially 19. It will be understood by those skilled in the art that maltodextrins with DEs above 20 are referred to as 'glucose syrups'.

Maltodextrins with DEs above 15 have lower average molecular weights than those with DEs of 15 or below. All maltodextrins are mixtures of polysaccharides with different chain lengths and maltodextrins with DEs above 15 have less of the larger molecular weight sugar units.

We have found that maltodextrins with lower DEs, such as those with a DE of 12 or below, contain longer polysaccharide chains (e.g. with greater than or equal to about 24 glucose units), which have a tendency to form helix structures that may form aggregates when presented in aqueous solutions along with other components, such as active ingredients and/or surfactants, like sucrose esters, giving rise to a turbid solution prior to spray-drying. This turbidity may give rise to stability and/or processability issues during manufacture, requiring the use of in-line filters.

Although we have found that the aforementioned turbidity problem may be alleviated to an extent by reducing the relative amount of maltodextrin that is included within a composition as described herein, which may be achieved by increasing the amount of other ingredients, such as other carrier materials (e.g. disaccharide), the active ingredient or certain additives, such as sucrose esters, the higher the molecular weight of the maltodextrin, the less that needs to be included, and the more e.g. disaccharide or sucrose ester that needs to be added to alleviate the turbidity.

If more sucrose ester is added in order to reduce this turbidity, more may need to be added than is necessary to provide an appropriate (e.g. physical, chemical and/or biological) effect, including an absorption-enhancing effect, as noted herein. Conversely, increasing the amount of disaccharide relative to maltodextrin in the carrier material may have a negative impact on Tg, and therefore the solid-state stability of the composition as noted herein.

We have found that such issues may be reduced, and possibly avoided altogether, by using different maltodextrins altogether, namely those with higher DEs, such as those with a DE above 15, e.g. DE 18, 20 or, more preferably 19.

Notwithstanding the above, maltodextrins that are suitable for use in powder compositions described herein should have a molecular weight that is nevertheless high enough such that, when it is employed in any given amount (in combination with a disaccharide or otherwise), it is capable of forming a suitable carrier material for the active ingredient, including the provision of an appropriate degree of physical stability.

Mixtures from any of the foregoing lists of disaccharides and/or polymeric materials (including maltodextrins) may be employed.

Whatever their proportions in the final mixture, compositions for inclusion in applicators of the invention include a spray-dried carrier material, which may be prepared by spray drying the relevant ingredients to form a composite carrier material either prior to spray-drying that carrier material along with the other essential ingredients to form a powder composition as described herein or, more preferably, is made in situ by spray-drying all of the essential components of that composition together.

We have in particular found that compositions that may be included in applicators of the invention comprising a combination of a disaccharide and a polymer (e.g. HPMC as defined herein) and/or, preferably, a dextrin and particularly a maltodextrin are capable of giving rise to an appropriate level of physical and chemical stability of compositions and active ingredients (particularly adrenaline and salts thereof). In fact, as described hereinafter, the degree of chemical stability in particular is remarkable in comparison, when compared to current commercially-available products comprising adrenaline for the treatment of allergic reactions, like the EpiPen.

A particularly preferred combination of carrier materials thus includes trehalose and a maltodextrin with a DE above 11, such as maltodextrin 12DE, or above 15, such as maltodextrin 19DE. We have found that such a combination of carrier materials can be spray-dried together along with an active ingredient and also, if present, an alkyl saccharide in appropriate proportions to produce a powder composition that possesses both the desired physical and chemical stability under normal storage conditions, as defined herein.

Combinations of adrenergic receptor modulators or salts thereof may be employed in compositions for inclusion in applicators of the invention.

Salts of adrenergic receptor modulators include any such salts that are known in the art and described for the drugs in question to in the medical literature, such as *Martindale—The Complete Drug Reference*, 40$^{th}$ Edition, Pharmaceutical Press, London (2020) and the documents referred to therein (the relevant disclosures in all of which documents are hereby incorporated by reference).

Otherwise, pharmaceutically acceptable salts include acid addition salts and base addition salts, which salts may be formed by conventional means, for example by reaction of a free acid or a free base form of the relevant active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include carboxylate salts, such as succinate, tartrate, formate, acetate, benzoate, oxalate, fumarate, maleate, xinafoate and the like, sulfonate salts, such as methanesulfonate, ethanesulfonate, toluenesulfonate and the like, halide salts, such as hydrochloride, hydrobromide and the like, sulfate and phosphate salts, such as sulfate or phosphate and the like.

Particular salts of adrenaline that may be mentioned include bitartrate salts.

When compositions for inclusion in applicators of the invention are made by a solvent-based process, as described hereinbefore, including by way of a process of spray-drying, this may result in the presence of active ingredient in a form in which it is no longer in the form of a crystalline salt because it is freely dispersed within, and encapsulated by, the carrier materials in an amorphous form. However, despite not being in the form of a crystalline salt, which it would normally be in the case of a typical solid-state mixture and/or powder composition, powder compositions as described herein may provide for little to no loss in chemical stability of that active ingredient under the normal storage conditions mentioned herein.

The amount of active ingredient that may be employed in a single dose of a composition that is included in an applicator of the invention must be sufficient so exert its pharmacological effect. For transmucosally- (e.g. sublingually-, buccally- and, particularly, intranasally-) administered compositions, that amount must not exceed about 100 mg in a single dose. Actual doses of the relevant active ingredients mentioned above include those that are known in the art and described for the drugs in question to in the medical literature, such as *Martindale—The Complete Drug Reference,* 40$^{th}$ Edition, Pharmaceutical Press, London (2020) and the documents referred to therein, the relevant disclosures in all of which documents are hereby incorporated by reference. However, compositions that are included in applicators of the invention may be found to exhibit good bioavailability and/or rapid absorption, resulting in a more rapid onset of action and/or higher plasma concentrations, compared to prior art compositions comprising the same active ingredient.

In this respect, pharmacologically-appropriate amounts of active ingredients in compositions that are included in applicators of the invention may be less than those referred to in the literature (vide supra). Such amounts may nevertheless be determined by the skilled person and may vary with the type and severity of the condition that is to be treated, and what will be most suitable for an individual patient. This is also likely to vary with the nature of the formulation, as well as the type and severity of the condition that is to be treated, as well as the age, weight, sex, renal function, hepatic function and response of the particular patient to be treated.

Depending upon the potency of the active ingredient, and upon the final formulation that is to be employed, the total amount of active ingredient that may be employed in a composition for inclusion in an applicator of the invention may be in the range of about 0.0002%, for example about 0.001%, such as about 0.01%, including about 0.1%, (e.g. about 1%, about 2% or about 5%), such as about 10% (e.g. about 20%) up to about 95%, such as about 75%, for example about 50%, e.g. about 40%, by weight based upon the total weight of the composition. This is independent of the number of separate doses of composition (which should be the same) that are initially present in the applicator of the invention.

For transmucosal, including pulmonary, buccal, sublingual or, preferably, intranasal, administration, appropriate doses of active ingredients (calculated as the free acid/base) per kg of body weight are in the range of about 1 μg/kg, such as about 2 μg/kg, including about 3 μg/kg, about 5 μg/kg or about 6 μg/kg up to about 15 μg/kg, such as about 13 μg/kg, including about 12 μg/kg, such as about 10 μg/kg or about 8 μg/kg.

In the alternative, appropriate doses of active ingredients (calculated as the free acid/base) per unit dosage are in the range of about 1 μg (e.g. about 10 μg, such as about 250 μg) to about 100 mg (e.g. about 80 mg), such as between about 1 mg and about 60 mg (e.g. about 3 mg, such as about 10 mg to about 50 mg), depending on the active ingredient that is employed.

When administered sublingually or, preferably, intranasally, specific doses of adrenaline are in the range of about 0.1 mg (e.g. about 0.5 mg) up to about 10 mg, such as up to about 5 mg, including up to about 3 mg or up to about 2 mg (e.g. about 1.5 mg, including about 1.2 mg, about 1 mg, or about 0.8 mg).

As mentioned hereinbefore, compositions that are included in applicators of the invention may also include, or may also be administered along with, one or more alkyl saccharides. Compositions that are included in applicators of the invention may be found in this respect to exhibit surprisingly good bioavailability and speed of absorption compared to corresponding compositions that do not include, for example, alkyl saccharides, and/or include different excipients that are known to act as surfactants.

Alkyl saccharides that may be employed include alkyl glycosides, which may be defined as any sugar joined by a linkage to an alkyl group, such as a $C_{7-18}$ alkyl glycoside. Alkyl glycosides thus may include alkyl maltosides (such as dodecyl maltoside), alkyl glucosides, alkyl sucrosides, alkyl thiomaltosides, alkyl thioglucosides, alkyl thiosucroses and alkyl maltotriosides. However, we prefer that the alkyl saccharide is a sugar ester.

Sugar esters that may be used in the powder compositions described herein include trisaccharide esters, such as raffinose esters, monosaccharide esters, such as glucose esters, galactose esters and fructose esters, and/or, preferably, disaccharide esters, such as maltose esters, lactose esters, trehalose esters and, in particular, one or more sucrose esters.

Sucrose esters that may be employed in compositions for inclusion in applicators of the invention have a hydrophilic-lipophilic balance value of between 6 and 20. The term 'hydrophilic-lipophilic balance' (HLB) is a term of art that will be well understood by those skilled in the art (see, for example, '*The HLB System: A Time-Saving Guide to Emulsifier Selection*', published by ICI Americas Inc, 1976 (revised 1980), in which document, Chapter 7 (pages 20-21) provides a method of how to determine HLB values). The longer the fatty acid chains in the sucrose esters and the higher the degree of esterification, the lower the HLB value. Preferred HLB values are between 10 and 20, more preferably between 12 and 20.

Sucrose esters thus include $C_{8-22}$ saturated or unsaturated fatty acid esters, preferably saturated fatty acid esters and preferably $C_{10-18}$ fatty acid esters and most preferably $C_{12}$ fatty acid esters. Particularly suitable fatty acids from which such sucrose esters may be formed include erucic acid, behenic acid, oleic acid, stearic acid, palmitic acid, myristic acid and lauric acid. A particularly preferred such fatty acid is lauric acid. Commercially-available sucrose esters include those sold under the trademark Surfhope® and Ryoto® (Mitsubishi-Kagaku Foods Corporation, Japan).

Sucrose esters may be diesters or monoesters of fatty acids, preferably monoesters, such as sucrose monolaurate. The skilled person will appreciate that the term 'monolaurate' refers to a mono-ester of lauric acid, and that the terms lauric acid ester' and 'laurate' have the same meaning and can therefore be used interchangeably. Commercially available sucrose monolaurate products are also sometimes referred to as 'sucrose laurate'. Commercially-available sucrose monolaurate (or sucrose laurate) products, such as Surfhope® D-1216 (Mitsubishi-Kagaku Foods Corporation, Japan), which may contain small amounts of diesters and/or higher sucrose esters, and minor amounts of other sucrose esters and free sucrose, are suitable for use in the invention. The skilled person will understand that any reference to a specific sucrose ester herein includes commercially available products comprising that sucrose ester as a principal component.

Preferred sucrose esters contain only one sucrose ester, which means that a single sucrose ester (e.g. a commercially-available sucrose ester product) contains a single sucrose ester as the/a principal component (commercially available products may contain impurities, for example a monoester product may contain small amounts of diesters and/or higher esters, such products may be considered to 'contain only one sucrose ester' in the context of the present invention). As used herein, the term 'principal component' will be understood to refer to the major component (e.g. greater than about 50%, such as about 70% weight/weight or volume/volume) in a mixture of sucrose esters, such as commonly commercially available surfactant products, which are typically sold with a certain range of ester compositions.

A particularly preferred sucrose ester is sucrose monolaurate.

When included within a composition for inclusion in an applicator of the invention, or in an applicator of the invention, amounts of alkyl saccharide that may be employed may be in the range of about 0.1% to about 10%, such as about 0.5% to about 5%, preferably about 0.75% to about 3% (e.g. to about 2%, such as about 1%), by weight, based upon the total weight of the composition.

Further, optional, additional excipients may be employed within, or administered along with, compositions for inclusion in applicators of the invention, including one or more (further) surfactants. Surfactants that may be mentioned include polyoxyethylene esters (e.g. Myrj™), including polyoxyl 8 stearate (Myrj™ S8), polyoxyl 32 stearate (Gelucire® 48/16), polyoxyl 40 stearate (Myrj™ S40), polyoxyl 100 stearate (Myrj™ 5100), and polyoxyl 15 hydroxystearate (Kolliphor® HS 15), polyoxyethylene alkyl ethers (e.g. Brij™), including polyoxyl cetostearyl ether (e.g. Brij™ CS12, CS20 and CS25), polyoxyl lauryl ether (e.g. Brij™ L9 and L23), and polyoxyl stearyl ether (e.g. Brij™ S10 and S20), and polyoxylglycerides (e.g. Gelucire®), including lauroyl polyoxylglycerides (Gelucire® 44/14) and stearoyl polyoxylglycerides (Gelucire® 50/13), sorbitan esters (e.g. Span™), including sorbitan monopalmitate (Span™ 40) and sorbitan monostearate (Span™ 60), polysorbates (Tweens™), including polysorbate 40 (polyoxyethylene (20) sorbitan monopalmitate), polysorbate 60 (polyoxyethylene (20) sorbitan monostearate) and polysorbate 20 (polyoxyethylene (20) sorbitan monolaurate), and sodium lauryl sulfate; and monoacyl glycerols (monoglycerides), such as 2-oleoylglycerol, 2-arachidonoylglycerol, monolaurin, glycerol monomyristate, glycerol monopalmitate, glyceryl hydroxystearate and, preferably, glycerol monostearate, glycerol monooleate (e.g. Cithrol®) and glycerol monocaprylate (e.g. Capmul®). Other surfactants may include dipalmitoylphosphatidylcholine (DPPC), lauryl lactate and poloxamers.

Other optional additional ingredients (excipients) that may be included within, or administered along with, compositions for inclusion in applicators of the invention, include isotonicity and/or osmotic agents (e.g. sodium chloride), sterols (or steroid alcohols), such as cholesterol and phytosterols (e.g. campesterol, sitosterol, and stigmasterol); antioxidants (e.g. sodium metabisulfite or, in addition, α-tocopherol, ascorbic acid, potassium ascorbate, sodium ascorbate, ascorbyl palmitate, butylated hydroxytoluene, butylated hydroxyanisole, dodecyl gallate, octyl gallate, propyl gallate, ethyl oleate, monothioglycerol, vitamin E polyethylene glycol succinate, or thymol); chelating (complexing) agents (e.g. edetic acid (EDTA), citric acid, tartaric acid, malic acid, maltol and galactose, including salt forms of any of these agents); preservatives (e.g. benzalkonium chloride or, in addition, benzyl alcohol, boric acid, parabens, propionic acid, phenol, cresol, or xylitol); viscosity modifying agents or gelling agents (such as cellulose derivatives, including hydroxypropylcellulose, methylcellulose, hydroxypropyl methylcellulose, carboxymethylcellulose, etc., starches and modified starches, colloidal silicon dioxide, aluminium metasilicate, polycarbophils (e.g. Noveon®), carbomers (e.g. Carbopol®) and polyvinylpyrrolidone); mucoadhesive polymers, such as carboxymethyl cellulose, modified cellulose gum and sodium carboxymethyl cellulose (NaCMC); starch derivatives, such as moderately cross-linked starch, modified starch and sodium starch glycolate; crosslinked polyvinyl pyrollidone, acrylic polymers, such as carbomer and its derivatives (Polycarbophyl, Carbopol®, etc.); polyethylene oxide (PEO); chitosan (poly-(D-glucosamine)); natural polymers, such as gelatin, sodium alginate, pectin; scleroglucan; xanthan gum; guar gum; poly co-(methylvinyl ether/maleic anhydride); and croscarmellose (e.g. croscarmellose sodium); pH buffering agents (e.g. citric acid, maleic acid, malic acid, or glycine, or corresponding salts thereof, such as sodium citrate); colouring agents; penetration enhancers (e.g. isopropyl myristate, isopropyl palmitate, pyrrolidone, or tricaprylin); other lipids (neutral and polar); aromatic carboxylic acids, such as benzoic acid optionally substituted with one or more groups selected from methyl, hydroxyl, amino, and/or nitro, for instance, toluic acid or salicylic acid; and, if appropriate, flavourings (e.g. lemon, peppermint powder or, preferably, menthol), sweeteners (e.g. neohesperidin, acesulfame K or, preferably, sucralose) and dyestuffs. Other excipients may include trisaccharides (e.g. raffinose) and mannitol, as well as pH adjusting agents (e.g. hydrochloric acid and sodium hydroxide).

Total amounts of such 'additional' excipients (including surfactants that are not an alkyl saccharide that may be present) that may be included within powder compositions described herein per se may also be up to about 15% (e.g. about 10%), such as up to about 5%, by weight, based on the total weight of the composition.

Total amounts of such 'additional' excipients that may be included within an applicator of the invention including one or more powder compositions for inclusion in an applicator of the invention, may be up to about 99.99%, such as up to about 99.9%, including up to about 99%, for example up to about 90%.

The skilled person will appreciate that, if any additional optional ingredients are included within compositions for inclusion in applicators of the invention, the nature of those ingredients, and/or the amounts of those ingredients that are included, should not have a detrimental effect on the Tg of the powder composition for the reasons described hereinbefore. In this respect, such optional ingredients may be incorporated in the spray-drying process (i.e. mixed together along with the active ingredient and the carrier material in the appropriate volatile solvent and then spray-dried), or may be included separately to the spray-dried plurality of particles.

In particular, in view of the enhanced chemical stability that compositions for inclusion in applicators of the invention provide for highly unstable active ingredients, such as adrenaline, and the fact that those compositions are primarily intended for use in the treatment of patients that are susceptible to allergic reactions (and thus potentially sensitised to certain chemicals), it is preferred that the relevant compositions are essentially free of such 'additional' excipients, in particular the antioxidants and/or the preservatives mentioned above, such as benzalkonium chloride, more especially sulphites, and/or chelating agents, such as EDTA.

In this respect, compositions for inclusion in applicators of the invention may consist essentially of a pharmacologically-effective dosage amount of the adrenergic receptor modulator, or salt thereof, the pharmaceutically-acceptable carrier material as defined herein and (optionally) the alkyl saccharide material as defined herein. If such a composition 'consists essentially of' the above ingredients, this will be understood to mean that that composition comprises only those ingredients, along with other features and/or components that do not materially affect the basic and novel characteristic(s) of the composition. Alternatively, in situations where the compositions for inclusion in applicators of the invention 'consist essentially of' those ingredients, this may be understood to mean that that composition comprises at least about 90%, such as at least about 95%, including at least about 97% (e.g. about 99%) by weight of those ingredients in total.

According to a further aspect of the invention, there is provided the applicators of the invention for use in medicine (human and veterinary), and thus in the treatment of patients in need of medical treatment of a condition that the relevant active ingredient is known to treat.

By 'treatment' of such conditions, we include the prophylaxis/prevention or the diagnosis of such conditions, in addition to therapeutic, symptomatic and palliative treatment.

Applicators of the invention are thus useful in the treatment of a variety of disorders, depending on the active ingredient(s) that is/are included in such a composition.

Applicators of the invention comprising dopamine may be employed in the correction of hemodynamic imbalances present in the shock syndrome due to myocardial infarction, trauma, endotoxic septicemia, open-heart surgery, renal failure and chronic cardiac decompensation (congestive failure); applicators of the invention comprising oxymetazoline may be employed as a decongestant; applicators of the invention comprising dobutamine may be employed in the treatment of e.g. heart failure; applicators of the invention comprising mirabegron may be employed in the treatment of overactive bladder syndrome; applicators of the invention comprising bronchodilators, such as albuterol (salbutamol), formoterol, levalbuterol, olodaterol, salmeterol and terbutaline may be employed in the treatment of asthma (including prevention of exercise-induced bronchospasm (EIB)), and/or chronic obstructive pulmonary disease (COPD; including bronchospasm associated therewith). Applicators of the invention comprising terbutaline may also be employed in the treatment of premature labour.

Applicators of the invention comprising norepinephrine may be employed in blood pressure control (and/or cardiac arrest) induced in certain acute hypotensive states, including sympathectomy, poliomyelitis, pheochromocytomectomy, spinal anaesthesia, myocardial infarction, septicemia, blood transfusion or drug reactions). Applicators of the invention comprising isoprenaline may be employed in the treatment of bradycardia, heart block and, occasionally, asthma.

In particular, applicators of the invention comprising adrenaline are useful in the treatment of, for example, heart failure (e.g. heart attacks) and/or, more particularly, allergic reactions, including extreme or severe allergic reactions, anaphylaxis and/or anaphylactic shock, for example characterised by severe drops in blood pressure as a consequence of a reaction to, for example, insect stings/bites, foodstuffs, drugs and/or other substances. Extreme and/or severe allergic reactions may further include sepsis and/or septic shock, which may be a reaction to, for example, infections by e.g. fungi, bacteria and/or viruses. Anaphylaxis and sepsis may further lead to dysfunction of organs, including organ failure and/or, ultimately, death.

Applicators of the invention comprising adrenaline are also useful in the treatment of, for example, any type-1 hypersensitivity reaction, in particular allergic asthma, allergic conjunctivitis, allergic rhinitis, anaphylaxis (including idiopathic anaphylaxis or exercise-induced anaphylaxis), angioedema, urticaria, eosinophilia, drug allergy (including antibiotic allergy), food allergy, allergic reactions to animal serums, insect bites and stings, diagnostic testing substances and other allergens; treatment of acute asthmatic attacks to relieve bronchospasm; treatment of systemic toxic responses (anaphylactoid reaction); treatment and prophylaxis of cardiac arrest and/or attacks of transitory atrioventricular heart block with syncopal seizures (Stokes-Adams Syndrome), including abrupt, transient loss of consciousness due to a sudden but pronounced decrease in the cardiac output, caused by a paroxysmal shift in the mechanism of the heartbeat; inducing increases in mean arterial blood pressure in adult patients with hypotension associated with septic shock; induction and maintenance of mydriasis during intraocular surgery; treatment of gastrointestinal and/or renal hemorrhage; treatment of superficial bleeding, premature labor, hypoglycemia, and cardiogenic, hemorrhagic, and traumatic shock; and/or treatment of croup (infections of the upper airways that obstructs breathing and causes a characteristic barking cough).

Applicators of the invention comprising adrenaline are particularly useful in the treatment and/or prevention (prophylaxis) of severe reactions, including anaphylaxis and sepsis and/or anaphylactic shock and septic shock as described above. Prevention and/or prophylaxis of these severe reactions may be effected by administration (including self-administration) of one or more compositions from an applicator of the invention to a patient at risk of such a reaction following exposure (or suspected exposure) to a relevant substance as described above, to which that patient is sensitive and/or has been sensitized.

According to three further aspects of the invention there is provided:
- an applicator of the invention comprising adrenaline for use in the treatment of an allergic reaction (for example by transmucosal, such as intranasal, administration of a composition contained therein);
- the use of a composition as described herein comprising adrenaline for the manufacture of an applicator for the treatment of an allergic reaction by administration of said composition transmucosally, such as an intranasally, via an applicator of the invention; and
- method of treatment of an allergic reaction, which method comprises the transmucosal, such as intranasal, administration of a composition via an applicator of the invention comprising adrenaline to a patient suffering from, or susceptible to, said condition.

There is further provided a method of treatment of an (e.g. severe) allergic reaction, including anaphylaxis, in a human patient, which comprises:
(a) identifying a human patient that is, or is in acute danger of, having such an allergic reaction, and
(b) administering a dosage amount that is suitable to treat said allergic reaction, of adrenaline, or a pharmaceutically-acceptable salt thereof in the form of a solid, amorphous mono-particulate powder as defined herein from an applicator of the invention, by actuating said applicator to dispense said dosage amount of adrenaline or salt thereof into a body cavity of said patient that includes a mucosal surface, so presenting said powder comprising said adrenaline or salt thereof at said mucosal surface to facilitate absorption of said adrenaline across said mucosal surface, and so treat or prevent said severe allergic reaction.

Compositions that are included in applicators of the invention are preferably administered intranasally. In this respect the applicator is preferably a suitable nasal applicator, or a dispenser means, which means is capable of administering a suitable dose of active ingredient in the form of one or more powder compositions as described herein to the nasal cavity.

A suitable nasal applicator of the invention should thus be capable of housing, and storing, the one or more doses of the relevant composition itself, or capable of being attached to a reservoir/container that houses and stores the one or more doses of said composition, and to do so without the consequence of a significant loss of physical and chemical integrity of the composition, including by way of ingress of water. In this way, the composition will be usable as soon as the applicator device is actuated by an end user (whether this is single dose or multiple dose usage), whereupon the applicator will deliver composition (e.g. powder) with an appropriate dose of active ingredient as defined herein to the nasal mucosa of a subject.

Appropriate applicator means have been described in the prior art. When used in the context of the present invention, compositions may be loaded into a reservoir that is attached to, or forms part of, such an applicator of the invention, whereupon it is contained until the applicator means, or dispenser, is actuated. Hereinafter the terms 'applicator', 'dispenser', 'device' 'applicator means', 'dispensing means', 'applicator device', 'dispensing device' and "insufflator' may be used interchangeably and mean the same thing.

An essential requirement of the applicator of the invention is that the reservoir that contains the solid, amorphous mono-particulate powder composition is opaque. Because of the unexpected stability of the compositions that are included in applicators of the invention, there is no need to inspect the contents of the reservoir (i.e. the powder composition) prior to administration or use. This is to be contrasted with commercially-available devices, such as the EpiPen, where the product label comprises a requirement to check the integrity of the contents prior to dispensing, for very good reasons, including the instability of the liquid solution compositions contained therein to heat, cold and light.

In view of this, the reservoir containing the powder compositions described herein is opaque, which will be understood by those skilled in the art to include 'not transparent or translucent, impenetrable to light, and/or not allowing light to pass through'.

Applicators of the invention therefore do not (and do not need to) comprise an inspection window through which the contents of the reservoir of the applicator can be observed and may, in this respect, be wholly opaque in their character, that is at least about 98%, such as at least about 99%, and particularly about 99.9% opaque, and/or no more than about 2%, such as no more than about 1% and particularly about 0.1% transparent, translucent and/or penetrable to light, to allow for inspection of reservoir's contents.

Such applicator means may thus also include a mechanism for expelling the powder composition as described herein from the reservoir through an exit (or 'dispensing') means, which dispensing means includes anything sized for placement within a human body cavity, such as a nostril, such as an appropriately-shaped nozzle.

The mechanism for expelling the powder may thus include a means for actuating the device, which may include breath-activated actuation or include an actuating means for generating a force upon actuation of the device by a user.

Thus, the applicator should be capable of providing a reproducible and sufficient amount of powder composition in a single administration step (and in a manner in which the device does not require 'priming'), that will provide a therapeutic dose of active ingredient.

Furthermore, because of the unexpected stability of the compositions that are included in applicators of the invention, and the lack of need to inspect the contents of the reservoir (i.e. the powder composition) prior to administration use, as soon as a patient has been identified as having, or as being in acute danger of having, an allergic reaction, the applicator of the invention may be used to administer an adrenergic receptor modulator (e.g. adrenaline), or pharmaceutically-acceptable salt thereof to a mucosal surface to treat, or prevent, said severe allergic reaction. Thus the administration step identified above may be carried out immediately after the identification step, without a delay, which delay may mean sufficient time to:

(i) inspect the composition contained within the reservoir of the applicator of the invention; and (ii) ascertain whether the relevant adrenergic receptor modulator- (e.g. adrenaline)-containing formulation may be safely administered to the patient to treat said allergic reaction effectively.

Nasal applicators/inhalation devices that may be employed to administer powder compositions as described herein include multiple-dose applications, such as metered dose inhalation devices (MDIs), dry powder inhalation devices (DPIs; including low, medium and high resistant DPIs) and soft mist inhalation devices (SMIs) that may be adapted based on technology that is known in the field of delivery of active ingredients to the lung.

In MDIs, powder compositions should be capable of forming a stable suspension when suspended in solvents that are typically employed therein, such as a propellant, which propellant has a sufficient vapour pressure to form aerosols upon activation of the delivery device (e.g. a hydrocarbon, a fluorocarbon, a hydrogen-containing fluorocarbon, or a mixture thereof).

However, if the nasal applicator is a single dose applicator from which a composition is dispensed following actuation, and is then disposed of after use, suitable applicator means or devices for delivering single doses of active ingredients include breath-assisted and blow-assisted devised (such as the Optinose®), as well as those described in U.S. Pat. Nos. 6,398,074, 6,938,798 or 9,724,713, the relevant disclosures in all of which documents are incorporated herein by reference. FIGS. 1 and 2 of the present application are based on FIG. 1 and FIG. 2, respectively, of U.S. Pat. No. 6,398,074, and FIGS. 3 to 7 are based on FIG. 19 to FIG. 23, respectively, of U.S. Pat. No. 9,724,713. Both are illustrations of applicators that may be employed to administer a powder composition intranasally.

In FIG. 1, the device comprises an upper body/dispenser head 1 incorporating an outlet channel 40 (i.e. part of the 'exit means' as hereinbefore described) and a gripping means 60 allowing the user to actuate the device. Inside the upper body/dispenser head 1 an element is mounted, designated in its assembly by reference number 2, that incorporates a reservoir 10 and an air chamber 22 for the air blast 20. It is possible for this element 2 to be produced in one piece with the body 1. A lower body 3 is also provided in order to be able to slide relative to the upper body 1 and relative to the element 2, the user exerting a push force on the lower body to actuate the device.

The reservoir 10 contains a single dose of a composition as described herein. The reservoir 10 has an air inlet 11 and a product outlet 15. A product retention device 2, comprising a grid that is permeable to air, is disposed in the air inlet 11 to keep the product in the reservoir 10 until the composition is dispensed. The product outlet 15 is blocked, preferably in a sealed fashion, by a closing ball 16, which is removed from its blocking position by the flow of air when the applicator is actuated and the product is being dispensed.

When a user actuates the device, a pressure is exerted on the plunger 25 in such a way that the piston 21 compresses the air 20 contained in the chamber 22. Since the grid 12 is permeable to air, the compression of the air in chamber 22 creates a blast of air that is transmitted to the reservoir 10 and consequently is applied to the closing ball 16 which is blocking the product outlet 15.

The dimensions of the closing ball 16 and its fixing at the reservoir product outlet 15 are such that the ball 16 is removed from its blocking position, when a minimum predetermined pressure is created through the reservoir 10 by way of a blast of the air 20.

The pre-compression created by the closing ball 16 ensures that when it is removed from its blocking position, the energy accumulated in the hand of the user is such that the piston 21 integral with the plunger 25 is propelled within the chamber 22 thereby creating a powerful blast of air 20, that is to say an air flow suitable to finely spray the dose of powder composition.

When this minimum pressure is reached, the ball is quickly moved towards the outlet channel 40 of the device and the flow of air 20 created by the blast expels substantially all of the dose of the composition that is contained within the reservoir 10.

Preferably, the outlet channel 40 has a diameter greater than the diameter of the closing ball 16 in order to allow the dose of product to be expelled through the outlet channel 40 by flowing around the ball 16. As shown in FIG. 2, which represents the same device after actuation, the channel 40 comprises a means 41 of arresting or fixing the ball 16 in order to prevent its expulsion out of the device when the product is being expelled.

A further embodiment of applicator means that may be employed to administer powder compositions as described herein intranasally is provided in U.S. Pat. No. 9,724,713 at column 7, line 50 to column 8, line 61 and FIGS. 19 to 23, which are reproduced as FIGS. 3 to 7 of the present application.

In this embodiment, the reservoir 10 is secured in the upper body/dispenser head 1 which includes the dispenser outlet channel 40 (i.e. part of the 'exit means' as hereinbefore described), which has gripping means or finger rest 60, which allows the user to actuate the device. A radial shoulder 67 (see FIG. 5) of the upper body/dispenser head 1 advantageously defines the assembled position of the reservoir 10 in said of the upper body/dispenser head 1.

The mechanical opening system includes a set of rods 61, 62, wherein a second rod portion 62 is pushed by said first rod portion 61 when the device is actuated. At the end of their actuation stroke, i.e. in the dispensing position, the set of rods 61, 62 co-operate with the closure element 16, which is spherical, in particular a ball as in the first embodiment discussed above, so as to expel it mechanically from its closed position.

In this embodiment, the piston 31 is separate from the first rod portion 61, and slides both relative to the air chamber 22 and to a cylindrical surface 614 that is secured to the first rod portion 61. FIG. 7 is a diagrammatic perspective view of the air expeller of the device in FIGS. 3 to 6, in its rest position.

The air chamber 22 may thus be cylindrical, and in its rest position is put into communication with the surrounding air at fluting or grooves 615 that are formed in said cylindrical surface 614 and that co-operate with the piston 21, in particular in its rest position. The piston 21 thus includes an inner lip 215 that slides in airtight manner over the cylindrical wall 614 during actuation, and that co-operates with said fluting 615 in its rest position. The piston 21 also includes an axial extension 216 that co-operates with a top edge 251 of the pusher element 25 (termed a 'plunger' in the first embodiment) that moves said piston 21 in the air chamber 22 during actuation.

A retainer member 42 is extended downwards by an axial extension 43 that comes into contact with the top axial end 610 of the first rod portion 61 during actuation.

In addition, in this embodiment, there is no outer body, but merely a cover 27 that is assembled on the bottom axial edge of the air chamber 22.

A spring 80 is provided between the radial flange 225 of the air chamber 22 and the part that forms the first rod portion 61 and the cylindrical surface 614, so as to return the air expeller automatically into its rest position after actuation.

The operating principle is as follows. In the rest position in FIG. 3, the reservoir 10 is closed in sealed manner by the retainer member 42 and by the closure element/ball 16. The air expeller is open to the atmosphere by co-operation between the inner lip 215 of the piston 21 and the fluting 615 of the cylindrical surface 614.

When it is desired to actuate the device, the user presses on the pusher element 25. During this initial stroke, the inner lip 215 of the piston leaves the fluting 615 so as to come to co-operate in airtight manner with the cylindrical surface 614, thereby closing the air chamber 22. At the same moment, the top edge 251 of the pusher element 25 comes into contact with the axial extension 216 of the piston 21, and the top axial end 610 of the first rod portion 61 comes into contact with the axial extension 43 of the retainer member 42.

Figure 4:
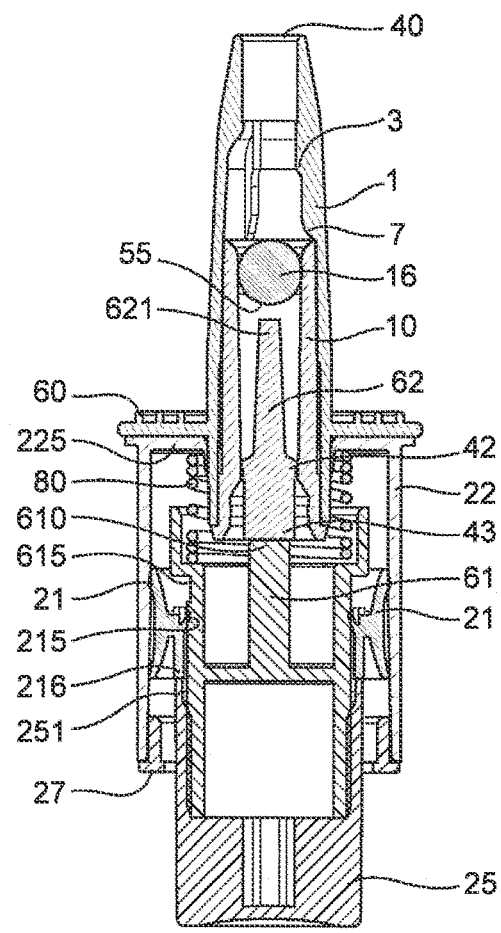

However, the top axial end 621 of the second rod portion 62 is still not in contact with the rounded surface 55 of the closure element/ball 16, as can be seen in FIG. 4.

Continued actuation thus simultaneously moves the piston 21 in the air chamber, thereby compressing the air contained therein, and moves the retainer member 42 away from its position of closing the reservoir 10. When the second rod portion 62 contacts the rounded surface 55 of the closure element/ball 16, said closure element/ball is expelled mechanically from its closed position, so as to enable the composition to be expelled under the effect of the air compressed by the air expeller.

Figure 5:
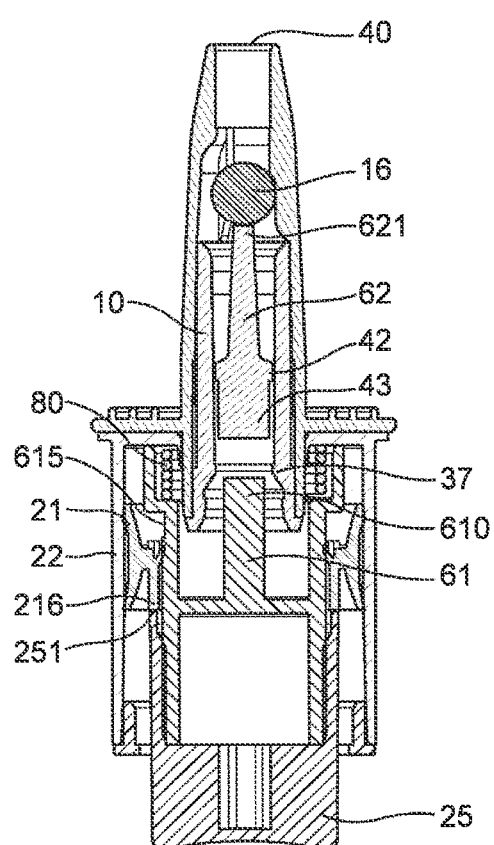

The dispensing position is shown in FIG. 5. As can be seen in FIG. 5, the retainer member 42 may become detached from the first rod portion 61 while the composition is being expelled under the effect of the compressed air provided by the air expeller. In this position, said closure element/ball is expelled out from the reservoir 10 so as to enable the fluid or powder to be dispensed under the effect of the compressed air. The closure element/ball 16 thus becomes jammed in splines 3 of the upper body/dispenser head 1, which splines prevent in particular any risk of said closure element/ball 16 being expelled out from said upper body dispenser head 1.

Figure 6:
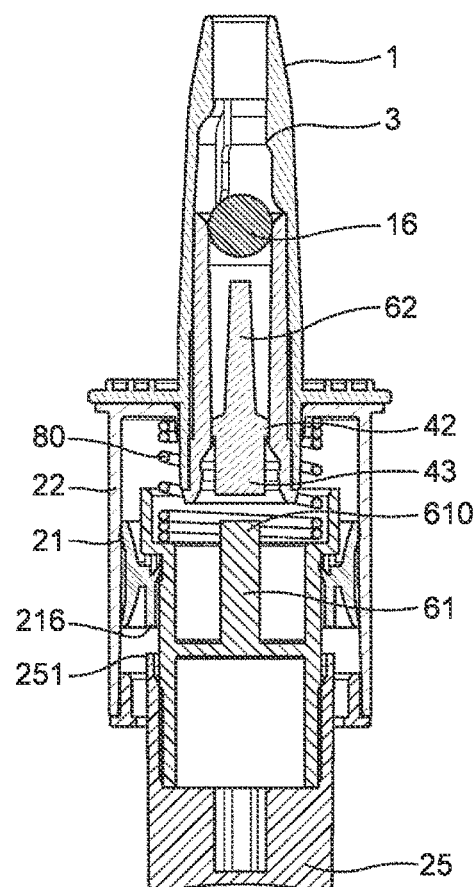
Figure 7:
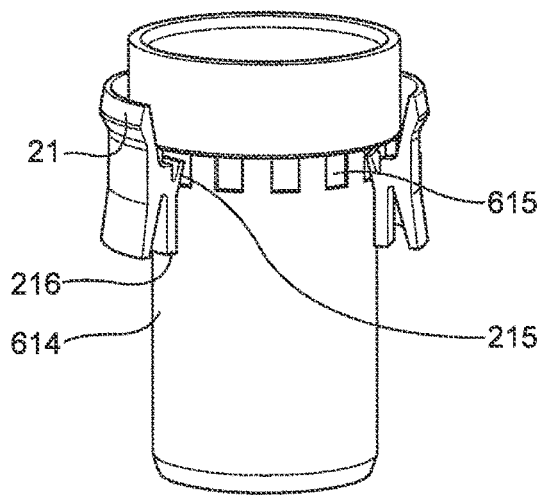

When the user relaxes the device, as shown in FIG. 6, the spring 80 that was compressed during actuation, returns the first rod portion 61 towards its rest position. This creates suction that sucks the closure element 16 and the retainer member 42 back towards, or close to, their closure positions. This thus blocks the path for new suction so as to avoid soiling the air expeller while it returns automatically into its rest position, with the empty reservoir still assembled on the air expeller. However, the piston 21 remains in its dispensing position as a result of friction with the air chamber 22 and of the suction created in the reservoir 30, such that the cylindrical surface 614 slides over the inner lip 215 of the piston until said inner lip co-operates once again with the fluting 615. At this moment, the air chamber 22 is once again in communication with the surrounding air, and suction is no longer created by the return into the rest position. The piston 21 is thus also entrained towards its rest position. This makes it possible to close the reservoir after use.

Optionally, the unit formed by the upper body/dispenser head 1 and the empty reservoir 10 could be removed from the air expeller and replaced by a new unit that includes a full reservoir.

Appropriate applicator devices that may be used include those available from Aptar Pharma, France (UDS Monopowder). See for example international patent applications WO 2022/208014 and WO 2021/005311. Other examples of applicator devices that may be used in conjunction with powder compositions according to the invention include those described in US patent application US 2011/0045088, U.S. Pat. No. 7,722,566 (see e.g. FIGS. 1 and 7) and U.S. Pat. No. 5,702,362 and international patent application WO 2014/004400, the relevant disclosures of which documents are hereby incorporated by reference.

According to a further aspect of the invention, there is provided a process for the manufacturing of an applicator of the invention, wherein said process comprises the step of loading said composition as defined herein into the reservoir that is within, or is adjunct, to said applicator.

According to another aspect, there is provided an applicator of the invention comprising one or more compositions according to the invention, which applicator may be actuated one or more times to deliver one or more compositions, each comprising an appropriate dose of active ingredient, upon each such actuation, which applicator comprises:

an outlet through which at least one composition is dispensed;

a means of externally generating a force (e.g. an air-flow) upon actuation of the applicator device by a user;

at least one (optionally replaceable and optionally opaque) reservoir that contains said one or more compositions, which reservoir is, or is capable of being placed, in direct or indirect communication with the dispenser outlet;

a displaceable, optionally reversible, sealing means in the applicator and/or the reservoir for retaining the one or more compositions within the reservoir until a composition is dispensed;

a mechanical opening system that co-operates with said sealing means such that a single composition is expelled mechanically by the forcing means when the applicator is actuated; and optionally, a mechanism for re-sealing the device and/or the reservoir to retain further compositions within the reservoir until a further composition is to be dispensed.

According to a still further aspect of the invention there is provided an applicator of the invention comprising a single dose of a composition according to the invention, suitable for dispensing that composition, which applicator comprises:

a dispenser outlet;

an air expeller for generating a flow of air while the device is being actuated, said air expeller including a piston that slides in an air chamber between a rest position and a dispensing position;

said piston slides in airtight manner within said air chamber;

at least one (e.g. opaque) reservoir that contains a dose of a composition according to the invention, said reservoir including an air inlet that is connected to said air expeller;

a composition outlet that is connected to said dispenser outlet;

said air inlet including a displaceable sealing means (e.g. a retainer member) for retaining the composition in the reservoir until the composition is dispensed;

said composition outlet being closed by a closure element that is fitted in the composition outlet of the reservoir;

said applicator further including a mechanical opening system that co-operates with said closure element so as to expel it mechanically from its closed position while the applicator is being actuated; and said piston of said air expeller, when in its rest position, co-operating in non-airtight manner with said air chamber.

In the latter aspect of the invention, it is preferred that:
(i) the air chamber within which said piston slides in airtight manner is substantially cylindrical;
(ii) the closure element is force fitted in the composition outlet of the reservoir;
(iii) said air chamber is in communication with the atmosphere in the rest position; and/or
(iv) said piston includes an inner lip that is suitable for co-operating with a cylindrical surface, said cylindrical surface includes fluting that co-operates in non-airtight manner with said inner lip of the piston in its rest position.

Such a nasal applicator or dispensing device is capable of providing for an appropriate and reproducible powder spray pattern and/or plume geometry that enables efficient delivery of said powder to the nasal cavity (e.g. a nostril).

In compositions that are employed in applicators of the invention, mean particle sizes may be presented as weight-, number-, or volume-, based mean diameters. As used herein, the term 'weight based mean diameter' will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). The term 'volume based mean diameter' is similar in its meaning to weight based mean diameter, but will be understood by the skilled person to include that the average particle size is characterised and defined from a particle size distribution by volume, i.e. a distribution where the existing fraction (relative amount) in each size class is defined as the volume fraction, as measured by e.g. laser diffraction. As used herein, the term 'number based mean diameter' will be understood by the skilled person to include that the average particle size is characterised and defined from a particle size distribution by number, i.e. a distribution where the existing fraction (relative amount) in each size class is defined as the number fraction, as measured by e.g. microscopy. Other instruments that are well known in the field may be employed to measure particle size, such as equipment sold by e.g. Malvern Instruments, Ltd (Worcestershire, UK), Sympatec GmbH (Clausthal-Zellerfeld, Germany) and Shimadzu (Kyoto, Japan).

Powder compositions that are employed in applicators of the invention will typically have a volume-based mean diameter (VMD) within the range of about 0.2 µm, such as about 0.5 µm (e.g. about 1 µm) up to about 1,000 µm (e.g. up to about 500 µm, such as about 400 µm or about 500 µm), and the appropriate particle size range may be selected based on the dosage form in which it is intended to include such compositions.

However, the skilled person will understand that, to allow for effective intranasal administration, powders will typically have a volume-based mean diameter (VMD) within the range of about 5 µm up to about 300 µm (e.g. up to about 200 µm). Depending on the applicator device that is employed, the VMD may be in the range of about 10 µm to about 100 µm, such as about 20 µm to about 60 µm.

Preferred particle size distributions for intranasal drug delivery may also include those in which the D10 is above about 3 µm and below about 75 µm (e.g. up to about 50 µm), such as greater than about 10 µm, and the D90 is between about 80 µm and about 1,000 µm (e.g. about 500 µm), such as less than about 100 µm. The skilled person will understand that the parameter 'D10' (or 'Dv(10)') means the size (or diameter) in a particle size distribution below which 10% of the total volume of material in the sample is contained. Similarly, the 'D90' (or 'Dv(90)') means the size below which 90% of the material is contained.

By powders having particle size distributions and VMDs within the above ranges, we include the bulk VMD and/or the emitted VMD, that is the particle size distribution when initially loaded into the device and/or when it is expelled therefrom, respectively.

Particle sizes may be measured by standard equipment, such as a dry (or a wet) particle size measurement technique, including dry dispersion technologies available from manufacturers such as Sympatec and Malvern.

Preferred particle shapes include spherical or substantially spherical, by which we mean that the particles possess an aspect ratio smaller than about 20, more preferably less than about 10, such as less than about 4, and especially less than about 2, and/or may possess a variation in radii (measured from the centre of gravity to the particle surface) in at least about 90% of the particles that is no more than about 50% of the average value, such as no more than about 30% of that value, for example no more than about 20% of that value.

Nevertheless, particles may be any shape, including irregular shaped (e.g. 'raisin'-shaped), needle-shaped, disc-shaped or cuboid-shaped, particles. For a non-spherical particle, the size may be indicated as the size of a corresponding spherical particle of e.g. the same weight, volume or surface area.

The spray angle of emitted (dispensed) powder composition from a nasal applicator according to the invention should preferably be less than about 90°.

Wherever the word 'about' is employed herein in the context of amounts, for example absolute amounts, such as doses, weights, volumes, sizes, diameters, aspect rations, angles, etc., or relative amounts (e.g. percentages) of individual constituents in a composition or a component of a composition (including concentrations and ratios), time-frames, and parameters such as temperatures, pressure, relative humidities, etc., it will be appreciated that such variables are approximate and as such may vary by ±10%, for example ±5% and preferably ±2% (e.g. ±1%) from the actual numbers specified herein. This is the case even if such numbers are presented as percentages in the first place (for example 'about 10%' may mean±10% about the number 10, which is anything between 9% and 11%).

Applicators of the invention, and compositions contained therein, have the advantage that they are capable of being stored over a wide range of temperatures and/or relative humidities. Thus, applicators of the invention may be subject to low temperatures (e.g. below freezing) without impacting the amount of active ingredient that is administered to a subject. Further, applicators of the invention may have the advantage that the powder compositions contained therein are more physically and chemically stable at all (including higher) temperatures than relevant prior art devices, such as the EpiPen.

Applicators of the invention further may also have the advantage that they provide for higher bioavailability of the active ingredient compared to prior art applicators or compositions, for example those comprising adrenaline. The compositions that are included in applicators of the invention may provide for this higher bioavailability alongside a more rapid absorption, which will likely lead to a more rapid onset of action than such prior art and/or commercially-available compositions, and thus meets a significant medical need.

The applicators, compositions, uses and methods described herein may also have the advantage that, in the treatment of the conditions for which the relevant active ingredient is known for, they may be more convenient for the first responder, physician and/or patient than, be more efficacious than, be less toxic than, have a broader range of activity than, be more potent than, produce fewer side effects than, have a lower inter-patient variability, or that it/they may have other useful pharmacological properties over, similar formulations or methods (treatments) known in the prior art, whether for use in the treatment of the aforementioned conditions by transmucosal, such as intranasal, administration or otherwise.

The invention is illustrated but in no way limited by way of the following examples with reference to the figures.

Comparative Example 1

Spray-Dried Epinephrine (Adrenaline) Formulation

Adrenaline bitartrate (0.729 g; Fisher Scientific, Sweden), along with α-D-lactose monohydrate (0.500 g; DFE Pharma, Germany), maltodextrin (Glucidex IT 12 DE; 1.247 g; Roquette, France), and sucrose monolaurate D-1216 (0.025 g; Mitsubishi-Kagaku Foods Corporation, Japan), were dispensed (in total 2.50 g) into a glass flask and dissolved in MQ-water (47.50 g) by stirring at room temperature.

The resultant mixture was fed into a spray-dryer (Pro-CepT, Belgium) equipped with an ultrasonic nozzle operating at 25 kHz. The feed rate of the spray-dryer was set at 3.0 g/minute, the inlet temperature was set at 180° C., the gas flow was set at 300 L/min, and the cyclone gas was set at 1.5 bar.

The resultant spray-dried powder was collected as a fine, dry, and free-flowing, with a nominal dose of 4 mg adrenaline free base in 25 mg powder.

The powder was analyzed for particle size distribution (PSD) by dry powder laser diffraction. The sample was dispersed with an Aero S dry dispersing unit (with compressed air at 0.5 bar) before sizing with a Mastersizer 3000 laser diffraction sensor (both Malvern Panalytical, UK), as shown in Table 1 below.

TABLE 1

| | |
|---|---|
| Dv(10) (μm) | 12.9 |
| Dv(50) (μm) | 23.9 |
| Dv(90) (μm) | 42.0 |

The PSD of the adrenaline formulation was well within a distribution suitable for nasal administration.

The assay and purity of the spray-dried adrenaline formulation was determined by HPLC/UV analysis. The assay was 99.7%, and the percentage of the total related substances (% RS) (i.e. impurities and degradation products) was less than 0.29%.

Comparative Example 2

Chemical Stability of Spray-Dried Powders

Amounts of between 105 and 115 mg of the spray-dried powders from Comparative Example 1 above was dispensed into 1.5 mL glass vials closed with screw-caps. Two vials were placed inside a climate cabinet at 40° C. and 75% relative humidity (40/75) and two vials were placed inside a climate cabinet at 25° C. and 60% relative humidity (25/60). For each storage condition, one vial was placed in the cabinet as it was, and one vial was further packaged in a heat-sealed aluminium sachet.

The chemical stability of the drug substance after up to 18 months, with total amounts of impurities and degradation products expressed as % RS, is summarized for the different compositions and packaging in Table 2 below, in which NA means 'not analysed'.

TABLE 2

| Test | Initial | 1 month | 3 months | 6 months | 18 months |
|---|---|---|---|---|---|
| | | Vial only (% RS) | | | |
| 40/75 | 0.29 | 2.27 | 8.22 | 25.27 | 41.50 |
| 25/60 | 0.29 | NA | 0.38 | 0.63 | 0.95 |
| | | Aluminium Sachet (% RS) | | | |
| 40/75 | 0.29 | 1.55 | 4.23 | 12.49 | 27.92 |
| 25/60 | 0.29 | NA | 0.37 | 0.87 | 2.42 |

Comparative Example 3

Pharmacokinetic Study in Dogs After Nasal and Intramuscular Administration of Adrenaline The purpose of the study was to obtain and evaluate basic pharmacokinetic profiles after nasal administration of the composition of Comparative Example 1, and after intramuscular administration of adrenaline in an aqueous solution.

The study was conducted in six Beagle dogs, three males and three females, of about 15-18 months age. The dogs were dosed in a cross-over dosing regimen to compensate for potential sequence effects. Dosing was always performed in the morning and the dogs had been fasted overnight (minimum 8 hours). Water was supplied ad libitum, and feed was given 4 hours after administration.

Each dog was given the composition of Comparative Example 1 nasally at a dose of 4 mg/animal (IN 4 mg), and adrenaline in an aqueous solution (1 mg/mL) at a dose of 0.3 mg/animal (IM 0.3 mg). The composition of Comparative Example 1 was administered intranasally by the specific intranasal device from Aptar Pharma, France (UDS Monopowder).

The aqueous solution of adrenaline was administered intramuscularly into the left back leg musculature (musculus quadriceps femoris). The wash-out period between each administration was 48 hours.

The in vivo part of the investigation was made in compliance with the European Convention for the Protection of Vertebrate Animals used for Experimental and other Scientific Purposes (ETS No. 123).

Blood samples were collected under conventional aseptic conditions by venepuncture from v. cephalica antebrachic or v. saphena from all dogs at specified time points. A volume of 1 mL was collected in plastic Vacuette® tubes containing K$_3$EDTA. The blood samples were kept on ice before centrifuged at 3500 rpm for 10 min at +4° C.

Plasma was extracted and transferred to pre-labelled cryovials containing Na metasulfite as an antioxidant and stored at −80° C. before transportation for bioanalysis. Scheduled sampling time points were: −5 (pre-dose), 2.5, 5, 10, 15, 20, 30, 45, 60 and 90 minutes after administration.

The frozen plasma samples were transported to Recipharm OT, Uppsala, Sweden, for bioanalysis. Plasma concentrations of adrenaline were determined by using HPLC-MS-MS analysis capable of measuring concentrations of adrenaline in dog plasma within the range of 0.05 to 100 ng/mL using adrenaline-D6 as the deuterated internal standard. The analytes were extracted from the sample plasma using protein precipitation with TCA. After centrifugation the supernatant was used for analysis.

All samples were analysed by first separating analytes using Acquity HSS T3 column (2.1 mm*100 mm, 1.7 µm) and subsequently detecting them using positive electrospray ionization and multiple reaction monitoring (MRM). Quantification was performed in the range 0.05 to 100 ng/mL.

Pharmacokinetic parameters were calculated by non-compartmental analysis using Phoenix WinNonlin (v8.0), and are presented in Table 3 below, in which $AUC_{last}$ is the area under the curve of plasma concentration versus time, up to the last sampling point; $C_{max}$ is the highest measureable concentration after administration and $t_{max}$ is the time to highest measureable concentration. The values presented in Table 3 are mean values of N=6.

TABLE 3

|  | $AUC_{last}$ (min*µg/L) | $C_{max}$ (µg/L) | $t_{max}$ (min) |
|---|---|---|---|
| Comparative Example 1 4 mg nasal administration | 143.28 | 10.76 | 10.83 |
| Aqueous sol. 0.3 mg i.m. administration | 72.15 | 1.83 | 34.58 |

Example 1

Epinephrine (Adrenaline) Formulations Produced by Spray-Drying in Air

Eight aqueous solutions (each 50 g; Formulations A to I, respectively) comprising dry matter compositions each with 0.364 g of adrenaline bitartrate, and with respective amounts of the excipients lactose monohydrate, maltodextrin (Glucidex IT 12 DE), HPMC (Methocel K3), sucrose monolaurate (D-1216), sodium metabisulfite, (Merck Chemical & Lifescience AB, Sweden) and/or disodium EDTA (Titriplex® III; Merck Chemical & Lifescience AB, Sweden), as shown in grams in Table 4 below, were spray dried by the general procedure described in Comparative Example 1 above, to produce fine, dry and free-flowing powders with a nominal dose of 1.0 mg adrenaline free base in 25 mg powder.

TABLE 4

| Formulation | Lactose | Maltodextrin | HPMC | Sucrose monolaurate | Na Metabisulfite | EDTA |
|---|---|---|---|---|---|---|
| A | 1.000 | 3.486 | 0 | 0.150 | 0 | 0 |
| B | 1.000 | 2.615 | 0.872 | 0.150 | 0 | 0 |
| C | 1.000 | 3.446 | 0 | 0.150 | 0.040 | 0 |
| D | 2.000 | 2.486 | 0 | 0.150 | 0 | 0 |
| E | 2.000 | 1.865 | 0.622 | 0.150 | 0 | 0 |
| F | 1.000 | 3.137 | 0.349 | 0.150 | 0 | 0 |
| G | 1.000 | 3.101 | 0.345 | 0.150 | 0.040 | 0 |
| H | 2.000 | 2.237 | 0.249 | 0.150 | 0 | 0 |
| I | 1.000 | 3.466 | 0 | 0.150 | 0 | 0.020 |

The PSD of the resultant powders was determined as described in Comparative Example 1 and is shown in Table 5 below and, again, was well within a distribution suitable for nasal administration.

TABLE 5

| Formulation | Dv(10) (μm) | Dv(50) (μm) | Dv(90) (μm) |
|---|---|---|---|
| A | 16.8 | 35.8 | 66.8 |
| B | 23.7 | 43.0 | 73.7 |
| C | 16.1 | 36.6 | 69.0 |
| D | 16.6 | 33.2 | 61.4 |
| E | NA | | |
| F | 20.5 | 42.2 | 73.9 |
| G | 18.9 | 38.2 | 68.9 |
| H | NA | | |
| I | 15.9 | 34.6 | 65.4 |

The initial assay and purity (expressed as % RS), as determined by HPLC/UV analysis, is presented in Table 6 below.

TABLE 6

| Formulation | Assay (%) | % RS |
|---|---|---|
| A | 105.1 | 0.23 |
| B | 105.9 | 0.21 |
| C | 101.7 | 0.25 |
| D | 104.5 | 0.25 |
| E | 100.6 | 0.32 |
| F | 101.1 | 0.16 |
| G | 101.6 | 0.23 |
| H | 101.9 | 0.29 |
| I | 101.5 | 0.23 |

A chemical stability experiment was carried out essentially as described in Comparative Example 2 above by packaging vials containing different adrenaline formulation in heat-sealed aluminium sachets together with a 4 Å molecular sieve desiccant, and storing them in a climate cabinet at 40/75.

The chemical stability after up to 12 months, with total amounts of impurities and degradation products expressed as % RS, is summarized for the different compositions in Table 7 below.

TABLE 7

| | Aluminium Sachet (% RS) | | | | |
|---|---|---|---|---|---|
| Formulation | Initial | 1 month | 3 months | 6 months | 12 months |
| A | 0.23 | 0.06 | 0.23 | 0.47 | 0.42 |
| B | 0.21 | 0.08 | 0.30 | 0.59 | 1.78 |
| C | 0.25 | 0.40 | 0.52 | 0.75 | 1.10 |
| D | 0.25 | 0.09 | 0.37 | 0.71 | 1.67 |
| E | 0.32 | 0.41 | 0.59 | 0.86 | 1.06 |
| F | 0.16 | 0.06 | 0.21 | 0.53 | 1.51 |
| G | 0.23 | 0.32 | 0.45 | 0.70 | 1.02 |
| H | 0.29 | 0.36 | 0.51 | 0.75 | 0.98 |
| I | 0.24 | 0.05 | 0.33 | 0.49 | 1.26 |

The observed changes in % RS for the easily degraded adrenaline show that chemical stability of drug substances is surprisingly good when formulated in the manner described herein.

One or more of Formulations A to I are loaded into the specific intranasal device from Aptar Pharma, France (UDS Monopowder) as described in Comparative Example 3 above for administration to human patients.

Example 2

Epinephrine (Adrenaline) Formulations Produced by Spray-Drying Under Nitrogen

Five aqueous solutions (each 50 g; Formulations J to N, respectively) comprising dry matter compositions each with 0.218 g of adrenaline bitartrate, and with respective amounts of the excipients lactose monohydrate, maltodextrin (Glucidex IT 12 DE), HPMC (Methocel K3), sucrose monolaurate (D-1216) and/or sodium metabisulfite, as shown in grams in Table 8 below, were spray dried by the general procedure described in Comparative Example 1 above, except that nitrogen was employed as the drying gas instead of air, to produce fine, dry and free-flowing powders with a nominal dose of 1.0 mg adrenaline free base in 25 mg powder.

TABLE 8

| Formulation | Lactose | Malto-dextrin | HPMC | Sucrose monolaurate | Na metabisulfite |
|---|---|---|---|---|---|
| J | 0.600 | 2.092 | 0 | 0.090 | 0 |
| K | 0.600 | 1.569 | 0.523 | 0.090 | 0 |
| L | 0.600 | 2.068 | 0 | 0.090 | 0.024 |
| M | 1.200 | 1.492 | 0 | 0.090 | 0 |
| N | 1.200 | 1.119 | 0.373 | 0.090 | 0 |

The initial assay and purity (expressed as % RS), as determined by HPLC/UV analysis, is presented in Table 9 below.

TABLE 9

| Example | Assay (%) | % RS |
|---|---|---|
| J | 103.1 | 0.05 |
| K | 102.8 | 0.06 |
| L | 103.6 | 0.14 |

TABLE 9-continued

| Example | Assay (%) | % RS |
|---|---|---|
| M | 101.0 | 0.09 |
| N | 101.2 | 0.10 |

A chemical stability experiment was carried out essentially as described in Comparative Example 2 above by packaging vials containing different adrenaline formulation in heat-sealed aluminium sachets together with a 4 Å molecular sieve desiccant, and storing them in a climate cabinet at 40/75.

The chemical stability after up to 12 months, with total amounts of impurities and degradation products expressed as % RS, is summarized for the different compositions in Table 10 below.

TABLE 10

| | % RS | | | | |
|---|---|---|---|---|---|
| Example | Initial | 1 month | 3 months | 6 months | 12 months |
| J | 0.22 | 0.27 | 0.45 | 0.77 | 1.07 |
| K | 0.28 | 0.32 | 0.46 | 0.91 | 1.07 |
| L | 0.39 | 0.44 | 0.58 | 0.89 | 1.21 |
| M | 0.37 | 0.50 | 0.57 | 0.80 | 0.95 |
| N | 0.39 | 0.40 | 0.50 | 0.75 | 0.82 |

One or more of Formulations J to N are loaded into the specific intranasal device from Aptar Pharma, France (UDS Monopowder) as described in Comparative Example 3 above for administration to human patients.

Example 3

Evaluation of Different Disaccharides and Maltodextrins

Nine aqueous solutions (each 50 g; Formulations O to W, respectively) comprising dry matter compositions each with 0.364 g of adrenaline bitartrate (Transo Pharm, Taiwan), and with respective amounts of disaccharides (lactose monohydrate (LT), trehalose (TH; Sigma-Aldrich (Merck), Sweden) sucrose (SU) and maltose (MT) (both Merck, Germany), maltodextrin (Glucidex IT 6DE, Glucidex IT 12 DE or Glucidex IT 19 DE; all Roquette, France) and sucrose monolaurate (D-1216; SM), as shown in grams in Table 11 below, were spray dried by the general procedure described in Comparative Example 1 above, to produce fine, dry and free-flowing powders with a nominal dose of 1.0 mg adrenaline free base in 25 mg powder.

TABLE 11

| Formul'n | LT | TH | SU | MT | IT 6 | IT 12 | IT 19 | SM |
|---|---|---|---|---|---|---|---|---|
| O | 0 | 1.106 | 0 | 0 | 0 | 3.431 | 0 | 0.152 |
| P | 0 | 0 | 1.076 | 0 | 0 | 3.411 | 0 | 0.154 |
| Q | 0 | 0 | 0 | 1.051 | 0 | 3.436 | 0 | 0.154 |
| R | 1.053 | 0 | 0 | 0 | 3.421 | 0 | 0 | 0.158 |
| S | 1.055 | 0 | 0 | 0 | 0 | 0 | 3.423 | 0.152 |
| T | 0 | 2.214 | 0 | 0 | 0 | 2.384 | 0 | 0.153 |
| U | 0 | 2.215 | 0 | 0 | 0 | 0 | 2.381 | 0.151 |
| V | 0.527 | 0 | 0 | 0 | 0 | 0 | 3.950 | 0.152 |
| W | 0 | 1.105 | 0 | 0 | 0 | 0 | 3.423 | 0.151 |

A chemical stability experiment was carried out essentially as described in Comparative Example 2 above by packaging vials containing different adrenaline formulation in heat-sealed aluminium sachets together with a 4 Å molecular sieve desiccant, and storing them in climate cabinets at 40/75 and at 50° C. at ambient RH in a conventional oven.

The chemical stability after up to 1 month (40/70) and up to 4 weeks (50° C.), with total amounts of impurities and degradation products expressed as % RS, is summarized for the different compositions in Table 12 below.

TABLE 12

| | | 40/75 | | | | |
|---|---|---|---|---|---|---|
| Formul'n | Initial | 1 month | 3 months | 6 months | 12 months | 50° C. 4 weeks |
| O | 0.02 | 0.06 | 0.31 | 0.58 | 0.91 | 0.23 |
| P | 0.02 | 0.06 | 0.31 | 0.56 | 0.79 | 0.26 |
| Q | 0.07 | 0.15 | 0.44 | 0.72 | 1.03 | 0.40 |
| R | 0.15 | 0.26 | 0.49 | 0.80 | 1.16 | 0.59 |
| S | 0.14 | 0.21 | 0.46 | 0.80 | 1.09 | 0.52 |
| T | 0.04 | 0.05 | 0.19 | 0.56 | 0.97 | 0.22 |
| U | 0.04 | 0.06 | 0.26 | 0.55 | 0.99 | 0.22 |
| V | 0.10 | 0.11 | 0.46 | 0.80 | 1.31 | 0.43 |
| W | 0.03 | 0.03 | 0.29 | 0.62 | 1.13 | 0.26 |

One or more of Formulations O to W are loaded into the specific intranasal device from Aptar Pharma, France (UDS Monopowder) as described in Comparative Example 3 above for administration to human patients.

Example 4

Storage Stability

Commercially available EpiPens (Meda Pharma GmbH & Co. KG, Germany) with approximately 9-12 months remaining shelf life upon arrival at the analysis laboratory were purchased from the pharmacy.

A chemical stability experiment was carried out essentially as described in Comparative Example 2, storing the EpiPens in a climate cabinet at 40/75. The chemical stability after up to 3 months, with total amounts of impurities and degradation products expressed as % RS, is summarized for the different compositions in Table 13 below.

TABLE 13

| Batch | Initial | 3 months | 6 months | 12 months |
|---|---|---|---|---|
| Epipen | 6.95 | 16.7 | 25.6 | 31.5 |
| Epipen Jr | 9.35 | 18.4 | 29.8 | 34.6 |

In a separate experiment, three Epipen autoinjectors, one in its original packaging (control), one with the outer box removed (original), and one being stripped from the plastic protective packaging, leaving only the product-containing glass syringe (syringe only), were placed in a light box and exposed to 1.2 million lux of UV light for 18 hours. Formulation S (see Example 1 above), and a Formulation W[1] (which had the same composition as Formulation W in Example 1 above, but was prepared on a larger scale) were also subjected to the same direct light exposure. The chemical stability, with total amounts of impurities and degradation products expressed as % RS, is summarized for the different compositions in Table 14 below.

TABLE 14

| Batch | Initial | 18 hours |
|---|---|---|
| Epipen (syringe only) | 2.90 | 3.51 |
| Epipen (original) | 2.90 | 3.82 |
| Epipen (control) | 2.90 | 3.68 |
| Formul'n S | 0.14 | 0.21 |
| Formul'n W[1] | 0.12 | 0.14 |

The enantiomeric purity of samples (Epipen, Formulation A from Example 1 above and Formulation W[1] (see above)) was also determined by chiral HPLC, according to a standard, USP-based method, after up to 6 months storage at 40/75.

Enantiomeric stability expressed as (% of S-adrenaline) is summarized for the different compositions in Table 15 below.

TABLE 15

| Batch | Initial | 1 month | 3 months | 6 months | 12 months |
|---|---|---|---|---|---|
| Epipen | 1.06 | ND | 2.31 | ND | 24.32 |
| Formul'n A | 2.5** | ND | ND | 2.58 | 2.52 |
| Formul'n W[1] | 0.21 | 0.30 | 0.45 | 0.61 | 0.73 |

**% S-adrenaline in the adrenaline raw material

Example 5

Evaluation of Different Doses of Adrenaline Using Trehalose and Different Maltodextrins Four aqueous solutions (each 50 g; Formulations X to AA, respectively) comprising dry matter compositions each with respective amounts of adrenaline bitartrate (Transo Pharm, Taiwan), trehalose, maltodextrin (Glucidex IT 12 DE or Glucidex IT 19 DE) and sucrose monolaurate (D-1216), as shown in grams in Table 16 below, were spray dried by the general procedure described in Comparative Example 1 above, to produce fine, dry and free-flowing powders with a nominal dose of 1.0 mg or 3.0 mg adrenaline free base in 25 mg powder.

TABLE 16

| Formul'n | Adrenaline bitartrate | TH | IT 12 | IT 19 | Sucrose monolaurate |
|---|---|---|---|---|---|
| X | 0.368 | 3.315 | 1.340 | 0 | 0.151 |
| Y | 1.091 | 1.103 | 0 | 2.661 | 0.150 |
| Z | 1.113 | 2.227 | 1.640 | 0 | 0.153 |
| AA | 1.090 | 2.210 | 0 | 1.628 | 0.151 |

A chemical stability experiment was carried out essentially as described in Comparative Example 2 above by packaging vials containing different adrenaline formulation in heat-sealed aluminium sachets together with a 4 Å molecular sieve desiccant, and storing them in a climate cabinet at 40/75.

The chemical stability after up to 1 month, with total amounts of impurities and degradation products expressed as % RS, is summarized for the different compositions in Table 17 below.

TABLE 17

| Formul'n | Initial | 1 month | 6 months |
|---|---|---|---|
| X | 0.02 | 0.15 | 0.52 |
| Y | 0.03 | 0.31 | 0.92 |
| Z | 0.03 | 0.25 | 1.12 |
| AA | 0.02 | 0.30 | 0.98 |

One or more of Formulations X to AA are loaded into the specific intranasal device from Aptar Pharma, France (UDS Monopowder) as described in Comparative Example 3 above for administration to human patients.

All formulations disclosed in Examples 1, 2, 3 and 5 above that included maltodextrins with DEs of less than 15 (e.g. 6 or 12) were found to be slightly turbid as observed by eye unless 40% disaccharide is used which clears the solution.

All formulations disclosed in in Examples 3 and 5 above in which maltodextrins with DEs of greater than to 15 (e.g. 19) were found not to be turbid as observed by eye.

Example 6

Lowest Measurable Tg Values

Between about 6 and 9 mg of samples of various formulations identified in Table 18 below were weighed into individual differential scanning calorimetry (DSC) crucibles, and allowed to equilibrate in an open vial at RH conditions as follows: 0%, 11%, 22%, 33% and 43%.

For the 0% RH condition, a desiccant with silica gel/molecular sieve was used. For the other four RH conditions, saturated aqueous salt solutions were used as hygrostats as follows: 11% RH—LiCl; 22% RH—$CH_3COOK$; 33% RH—$MgCl_2$; 43% RH—$K_2CO_3$.

Each sample was then closed with a lid and analysed using modulated DSC to determine the apparent glass transition temperature (Tg).

DSC was carried out using a Netzsch DSC 204F1 instrument. The glass transition temperatures (Tg values) for each of the investigated formulations were determined using hermetically-sealed ampoules or a punched lid (0% RH). A hermetic lid was adapted and crimped onto hermetic pans for all the samples stored together with saturated aqueous salt solutions.

For the 0% RH condition, conventional DSC pans were used with lids in which a 0.3 mm hole was punched in the lid by the instrument. This was performed to facilitate a perfectly dry condition during the experiment where the samples are surrounded by nitrogen in the instrument and potentially absorbed moisture allowed to be released during the heating phase.

For the rest of the samples, the DSC lid was gas-tight throughout the DSC run. Since the gas space around the sample in the cup was very small, the amount of water present in the gas phase at equilibrium was strictly limited, and the experimental time was very short, it can be assumed that equilibrium water is maintained in the sample throughout the experiment, despite elevation of the temperature for all Tg values at the lower temperature range.

Each sample was analysed using a modulated temperature profile with an average heating rate of 5 K/min, a modulation period of 20 seconds and an amplitude of ±0.5 K. The minimum temperature at the start was 0° C., and the maximum temperature was 200° C. The temperature was kept at 0° C. for 15 minutes before heating.

Formulations prepared according to Examples 3 and 5 above were analysed and the Tg measurements are presented in Table 18 below.

TABLE 18

| | Tg (° C.) | | | | |
|---|---|---|---|---|---|
| Formulation | 0% RH | 11% RH | 22% RH | 33% RH | 43% RH |
| O | 87 | 64 | 58 | 54 | 48 |
| T | 89 | 70 | 59 | 47 | 42 |
| U | 87 | 65 | 57 | 46 | 36 |
| V | 87 | 74 | 67 | 56 | 49 |
| W | 88 | 71 | 56 | 51 | 46 |
| X | 82 | 60 | 52 | 43 | 31 |
| Y | 80 | 61 | 50 | 45 | 36 |
| Z | 74 | 60 | 49 | 43 | 33 |
| AA | 77 | 66 | 49 | 40 | 30 |

As a comparison, Formulation D, prepared according to Comparative Example 4 above, displayed a Tg at 0% RH of 78° C., at 11% TH of 64° C.; and at 33% RH of 59° C.

All of the above values are deemed acceptable.

Example 7

Intranasally-Administered Epinephrine—Pharmacokinetic Study (Healthy Volunteers)

Four 1 mg epinephrine nasal powder formulations (Formulations 1-4) were made essentially as described in Comparative Example 1 above (with the exception that the feed rate of the spray-dryer was set at 4.0 g/minute), but with varying amounts of trehalose and maltodextrin, as shown in Table 19 below.

TABLE 19

| | Formulation | | | |
|---|---|---|---|---|
| | 1 (mg/dose) | 2 (mg/dose) | 3 (mg/dose) | 4 (mg/dose) |
| Epinephrine tartrate | 1.82[1] | 1.82[1] | 1.82[1] | 1.82[1] |
| Trehalose | 5.00 | 10.00 | 14.00 | 18.75 |
| Sucrose laurate | 0.75 | 0.75 | 0.75 | 0.75 |
| Maltodextrin | 16.43 | 11.43 | 7.43 | 2.68 |
| Water from process | 1.00 | 1.00 | 1.00 | 1.00 |
| Total weight | 25 | 25 | 25 | 25 |

[1]Corresponds to 1.00 mg epinephrine free base.

A Phase I clinical study was performed with the primary objective to determine the bioavailability of the four epinephrine nasal powder relative to the reference commercial product EpiPen®. ('Ref'; epinephrine, intramuscular injection, 0.3 mg; Meda AB, Solna, Sweden).

Secondary objectives were to characterize additional PK parameters; compare the pharmacodynamic (PD) effects on systolic/diastolic blood pressure (SBP/DBP), mean arterial blood pressure (MAP), and heart rate (HR) between treatments; and assess the safety and tolerability of the investigational formulations.

The study was a randomised sequence, single-centre, open label, 5-period crossover study to evaluate the comparative bioavailability of the 4 powder formulations to epinephrine intramuscular injection in healthy subjects. Each subject received each of Formulations 1 to 4, as well as Ref in a sequence according to a pre-set randomisation schedule, separated by a 24-hour wash-out period.

Subjects were randomised immediately before administration of the first dose of the relevant investigational medicinal product (IMP) or Ref (if used). A computer-generated randomisation schedule was used to allocate subject numbers to 1 of 10 treatment sequences.

About 65 subjects were screened for inclusion in the study up to 28 days before dosing. 40 eligible subjects (healthy male and non-pregnant, non-lactating, female subjects between 18 and 55 years of age with a body mass index between 18.5 and 30.0 kg/m$^2$) were admitted to the clinical unit on the evening prior to IMP administration (Day −1) and remained on site until being discharge at 24 hours post-final dose (after receiving all 5 treatments).

Formulations 1 to 4 were administered intranasally by the specific intranasal device from Aptar Pharma, France (UDS Monopowder). Subjects received IMPs or Ref in the morning of Days 1, 2, 3, 4 and 5, with an appropriate interval between subjects based on logistical requirements (approximately 10 minutes). IMPs were administered to alternate nostrils on each day of dosing. A follow-up phone call took place 3 to 5 days after the final dose to ensure the ongoing wellbeing of the subjects.

Of the 40 subjects that were enrolled, 37-39 received all IMPs and Ref. For analysis purposes, 37-39 subjects were included in the safety population, safety analysis dataset and the PK population.

Plasma concentrations of epinephrine were analysed using non-compartmental analysis methods to obtain estimates of PK parameters as set out below:

| Parameter | Definition |
|---|---|
| AUC(t) | area under the curve from time 0 to last measurable concentration |
| AUC(inf) | area under the curve from time 0 extrapolated to infinity |
| AUC(0-10) | area under the curve from time 0 to 10 min |
| AUC(0-20) | area under the curve from time 0 to 20 min |
| AUC(0-30) | area under the curve from time 0 to 30 min |
| AUC(0-45) | area under the curve from time 0 to 45 min |
| AUC(0-60) | area under the curve from time 0 to 60 min |
| Cmax | maximum observed concentration |
| T(100 pg/mL) | time to the concentration of 100 pg/ml |
| T(200 pg/mL) | time to the concentration of 200 pg/ml |
| T(>100 pg/mL) | time above the concentration of 100 pg/ml |
| T(>200 pg/mL) | time above the concentration of 200 pg/ml |
| T | time of maximum observed concentration |
| T½ | apparent elimination half-life |

The following parameters were used to analyse the PD effect.

| Parameter | Definition |
|---|---|
| AUECt (mmHg*h (for BP), beats (for HR) | area under the effect curve from time 0 to last measurable concentration |
| AUEC20 | area under the effect curve from time 0 to 20 min |
| AUEC45 | area under the effect curve from time 0 to 45 min |
| AUEC90 | area under the effect curve from time 0 to 90 min |
| Emax | maximum observed effect (mmHg/bpm) |
| Tmax (min) | time to maximum observed effect |

The evaluation of safety parameters comprised analysis of adverse events (AEs), local tolerability, laboratory evaluations, vital signs, electrocardiogram (ECG) and physical examination findings.

Log-transformed exposure parameters (AUCs and Cmax) were compared with standard methods to assess relative bioavailability. A single mixed effects model was fitted for each parameter to obtain estimates of geometric mean ratios (GMRs) and corresponding confidence intervals (CIs) for all treatment comparisons of interest. Models included terms for actual treatment received, study day (i.e. period) and planned sequence fitted as fixed effects and subject within sequence fitted as a random effect. Results were presented back-transformed to the linear scale. The following comparisons were of interest:

Relative bioavailability compared to Ref: IMP:Ref GMRs for AUC(0-t), AUC(0-inf) and Cmax were determined Partial AUC:s compared to Ref: IMP:Ref GMRs for AUC(0-10), AUC(0-20), AUC(0-30), AUC(0-45), and AUC(0-60 min) were determined For PD parameters, comparisons were made using arithmetic mean differences and corresponding 90% confidence intervals.

Results

Figure 8:
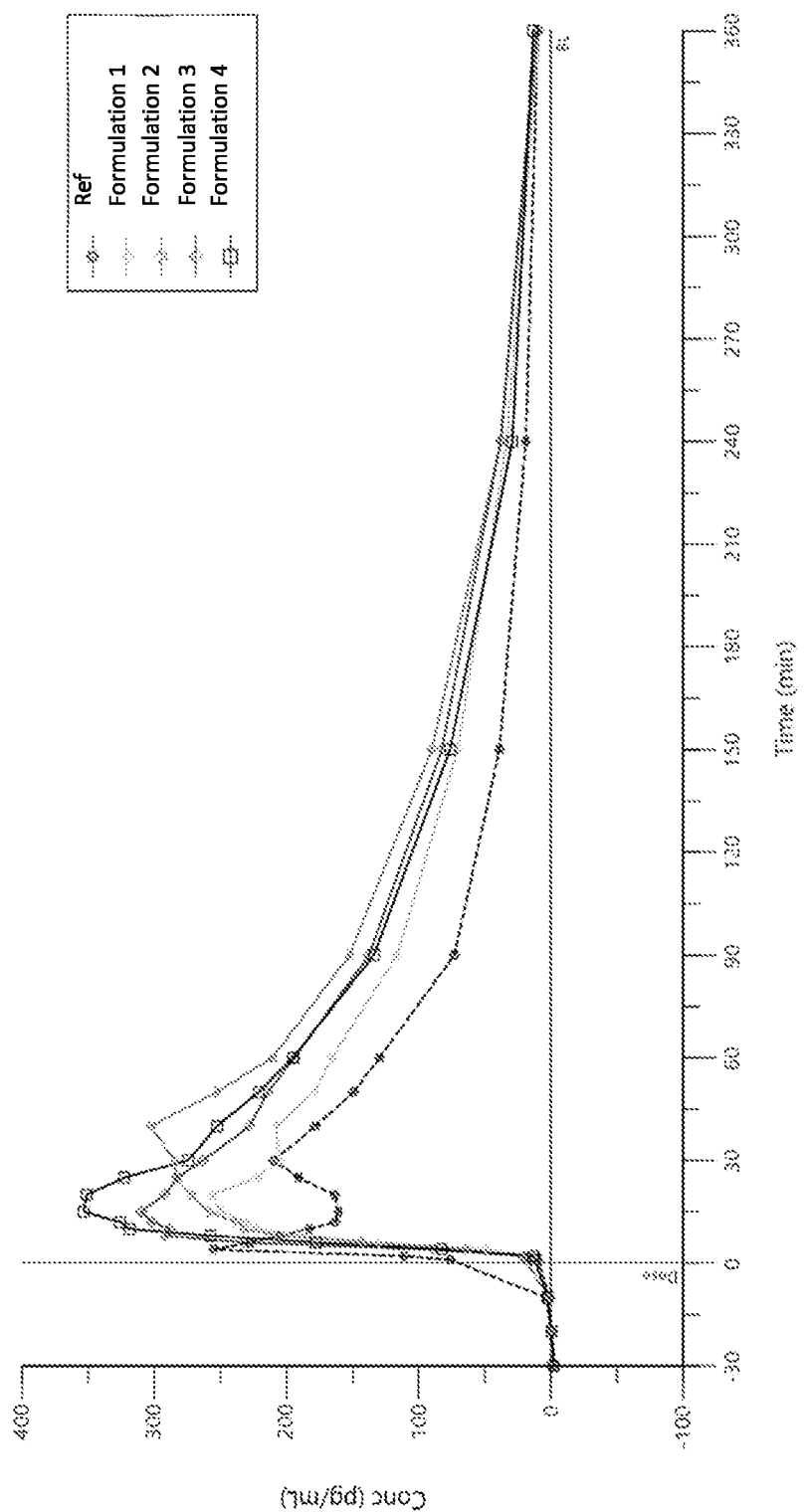
FIG. 8 shows epinephrine plasma concentrations vs time (linear scale; arithmetic mean), by treatment, as obtained in a Phase I clinical study.

Arithmetic mean epinephrine plasma concentrations vs time, by treatment (linear scale) are shown in FIG. 8. Geometric mean epinephrine plasma concentrations vs time, by treatment (semi log scale) are described in Table 20 below.

TABLE 20

| Parameter | Formulation 1 | 2 | 3 | 4 | Ref |
|---|---|---|---|---|---|
| N | 37 | 38 | 39 | 39 | 37 |
| AUC(t) (pg*h/mL)[a] | 388 (59.3) | 480 (68.7) | 478 (62.1) | 459 (67.1) | 308 (47) |
| AUC(0-20) (pg*h/mL) (%)[a] | 38.4 (133) | 40.6 (143) | 56.7 (97.1) | 56.6 (110) [n = 18] | 47.3 (74) |
| Cmax (pg/ml)[a] | 269 (82.4) | 305 (98.1) | 377 (73.0) | 361 (99.6) | 325 (55.8) |
| T(100 pg/mL) (min)[a] | 7.08 (94.33) n = 35 | 5.65 (102.72) n = 36 | 5 (75.9) n = 38 | 5.53 (67.85) n = 38 | 2.15 (151.96) n = 36 |
| T(>100 pg/mL) (min)[b] | 87.13 (0-296.63) | 138.27 (0-287.58) | 123.47 (0-285.19) | 120.4 (0-357.86) | 73.58 (0-209.91) |
| T(200 pg/mL) (min)[a] | 8.74 (85.79) n = 26 | 8.84 (113.37) n = 29 | 7.35 (94.97) n = 33 | 8.2 (71.16) n = 35 | 3.9 (168.47) n = 30 |
| T(>200 pg/mL) (min)[b] | 18.69 (0-105.53) | 48.52 (0-189.18) | 44.28 (0-140.72) | 35.82 (0-159.08) | 18.29 (0-242.75) |
| Tmax (min)[a] | 21.1 (99.2) | 24.3 (84) | 21.4 (103) | 20.5 (76.6) | 10.5 (202) |

N = number of subjects in the dataset; n = number of subjects with an observation.
[a]Geometric mean (geometric CV %);
[b]Median (range)

The analysis of relative bioavailability (GMR, 90% CI) is shown in Table 21 below.

TABLE 21

| Comparison | AUC(0-t) (%) | Cmax (%) |
|---|---|---|
| 1: Ref | 129.72 (108.6, 154.95) | 84.91 (66.22, 108.87) |
| 2: Ref | 161.47 (135.42, 192.54) | 97.60 (76.21, 125.01) |
| 3: Ref | 157.29 (132.07, 187.32) | 117.38 (91.79, 150.1) |
| 4: Ref | 148.98 (125.21, 177.26) | 112.08 (87.7, 143.24) |

All IMP Formulations displayed higher overall plasma exposure, and similar or higher peak plasma exposure, of epinephrine compared to Ref.

Table 22 below shows descriptive statistics of epinephrine partial AUCs (as geometric means; geometric CV %) by treatment. Table 23 shows partial AUCs for Formulations 1-4 compared to Ref (GMR, 90% CI).

TABLE 22

| Parameter | Formulation 1 | 2 | 3 | 4 | Ref |
|---|---|---|---|---|---|
| AUC(0-10 min) (pg · h/mL) | 10.1 (154) | — | 15.2 (194) | 15.3 (112) | 22.5 (96.6) |
| AUC(0-20 min) (pg · h/mL) | 38.4 (133) | 40.6 (143) | 56.7 (97.1) | 56.6 (110) | 47.3 (74) |
| AUC(0-30 min) (pg · h/mL) | 67.1 (115) | 75.9 (122) | 96.6 (84.7) | 93.6 (109) | 75.3 (66.6) |
| AUC(0-45 min) (pg · h/mL) | 111 (92.4) | 130 (113) | 149 (76.6) | 145 (102) | 116 (61.8) |
| AUC(0-60 min) (pg · h/mL) | 146 (84.6) | 178 (105) | 196 (70.3) | 191 (96.8) | 149 (59.1) |

TABLE 23

| Comparison | AUC (0-10) (%) | AUC (0-20) (%) | AUC (0-30) (%) | AUC (0-45) (%) | AUC (0-60) (%) |
|---|---|---|---|---|---|
| 1: Ref | 45.77 (32.21, 65.04) | 82.9 (61.20, 112.28) | 91.35 (69.09, 120.79) | 98.17 (76.22, 126.45) | 102.38 (80.44, 130.32) |
| 2: Ref | 53.03 (37.31, 75.38) | 88.83 (65.68, 120.15) | 104.62 (79.22, 138.17) | 117.37 (91.21, 151.03) | 126.19 (99.40, 160.20) |
| 3: Ref | 66.55 (47.02, 94.18) | 119.67 (88.64, 161.55) | 128.84 (97.73, 169.85) | 130.21 (101.35, 167.28) | 134.88 (106.41, 170.96) |
| 4: Ref | 68.19 (48.21, 96.44) | 119.85 (88.84, 161.68) | 125.14 (95.00, 164.85) | 125.98 (98.14, 161.70) | 129.58 (102.32, 164.10) |

All IMP formulations displayed similar or higher plasma exposure of epinephrine than Ref after the first 20 minutes after dosing.

The effect of all IMP formulations and Ref on systolic (Table 24) and diastolic (Table 25) blood pressure are shown below.

TABLE 24

| Parameter | Formulation 1 | 2 | 3 | 4 | Ref |
|---|---|---|---|---|---|
| Emax | 18.4 (8.36) | 19.1 (10.5) | 18.4 (10.6) | 20.7 (8.72) | 11.2 (6.61) |
| Tmax | 25 (1, 361) | 20 (1, 241) | 25 (1, 360) | 30 (4, 362) | 6 (1, 240) |
| Emin | -4.28 (6.81) | -3.81 (5.68) | -4.74 (6.79) | -5.44 (6.61) | -8.37 (6.05) |
| Tmin | 90 (1, 360) | 150 (1, 360) | 150 (1, 362) | 238 (1, 361) | 90 (1, 360) |
| AUEC20 min | 2.95 (2.65) | 2.8 (2.93) | 3.07 (3.2) | 3.08 (2.8) | 0.62 (1.57) |
| AUEC45 min | 7.4 (5.17) | 7.08 (6.18) | 6.98 (6.15) | 7.42 (5.83) | 1.13 (3.47) |
| AUEC90 min | 13.82 (9.37) | 12.52 (10.57) | 12.37 (10.03) | 13.92 (9.63) | 1.1 (6.98) |
| AUECt | 27 (36.17) | 23 (32.33) | 25.67 (31.33) | 27.17 (39.83) | -6.35 (37.17) |

TABLE 25

| Parameter | Formulation 1 | 2 | 3 | 4 | Ref |
|---|---|---|---|---|---|
| Emax | 13.6 (8.82) | 12.4 (7.78) | 11.4 (8.03) | 12.1 (9.2) | 5.78 (3.97) |
| Tmax | 25 (1, 361) | 15 (1, 360) | 10 (1, 362) | 12 (1, 360) | 20 (1, 360) |
| Emin | -4.81 (4.49) | -4.81 (4.77) | -4.7 (4.77) | -5.76 (5.09) | -8.75 (5.62) |
| Tmin | 40 (1, 361) | 60 (1, 360) | 160 (1, 362) | 90 (6, 360) | 17.5 (2, 360) |
| AUEC20 min | 1.41 (2.08) | 1.1 (1.9) | 1.11 (1.8) | 1.11 (1.9) | -0.77 (1.11) |
| AUEC45 min | 3.27 (4.37) | 2.23 (4.35) | 2.22 (3.93) | 2.4 (4.12) | -1.95 (2.38) |
| AUEC90 min | 5.97 (8.57) | 3.62 (8.58) | 3.63 (7.13) | 4.58 (8.35) | -3.88 (4.77) |
| AUECt | 14.78 (27.67) | 9.93 (27) | 10.27 (26.83) | 7.23 (29.33) | -9.65 (22.17) |

The effect of all IMP formulations and Ref on mean arterial blood pressure is shown in Table 26, and the effect on heart rate is shown in Table 27, respectively, below.

TABLE 26

| Parameter | Formulation 1 | 2 | 3 | 4 | Ref |
|---|---|---|---|---|---|
| Emax | 13.8 | 12.6 | 12.2 | 13.4 | 6.2 |
|  | (7.72) | (8.02) | (8.12) | (8.46) | (4.74) |
| Tmax | 15 | 20 | 20 | 15 | 7 |
|  | (1, 361) | (1, 245) | (1, 365) | (1, 362) | (1, 360) |
| Emin | −3.54 | −3.09 | −3.50 | −4.40 | −7.18 |
|  | (4.54) | (4.01) | (4.65) | (4.9) | (4.92) |
| Tmin | 60 | 90 | 90 | 150 | 55 |
|  | (1, 361) | (2, 360) | (1, 362) | (1, 360) | (2, 360) |
| AUEC20 min | 1.92 | 1.67 | 1.77 | 1.77 | −0.31 |
|  | (2.12) | (2.08) | (2.15) | (2.00) | (1.11) |
| AUEC45 min | 4.65 | 3.85 | 3.8 | 4.07 | −0.92 |
|  | (4.33) | (4.62) | (4.42) | (4.35) | (2.45) |
| AUEC90 min | 8.58 | 6.58 | 6.53 | 7.7 | −2.22 |
|  | (8.37) | (8.53) | (7.45) | (8.28) | (4.85) |
| AUECt | 18.83 | 14.28 | 15.4 | 13.85 | −8.55 |
|  | (27.33) | (25.67) | (25.00) | (30.00) | (25.00) |

TABLE 27

| Parameter | Formulation 1 | 2 | 3 | 4 | Ref |
|---|---|---|---|---|---|
| Emax | 15.7 | 15.9 | 16.8 | 19.1 | 14.9 |
|  | (5.71) | (6.93) | (9.09) | (8.44) | (6.02) |
| Tmax | 10 | 12 | 12 | 12 | 8 |
|  | (1, 240) | (1, 240) | (4, 360) | (1, 360) | (1, 360) |
| Emin | −4.64 | −5.87 | −5.13 | −4.51 | −6.68 |
|  | (5.05) | (4.17) | (4.1) | (4.97) | (3.97) |
| Tmin | 150 | 150 | 150 | 90 | 150 |
|  | (1, 361) | (1, 361) | (1, 362) | (1, 360) | (1, 361) |
| AUEC20 min | 2.25 | 2.1 | 2.27 | 2.73 | 1.43 |
|  | (1.72) | (1.62) | (1.95) | (1.97) | (1.22) |
| AUEC45 min | 4.58 | 4.08 | 4.73 | 5.52 | 2.98 |
|  | (3.70) | (3.85) | (4.35) | (4.72) | (2.92) |
| AUEC90 min | 7.87 | 7.10 | 8.42 | 9.85 | 4.47 |
|  | (7.80) | (7.17) | (9.02) | (9.55) | (6.13) |
| AUECt | 16.22 | 7.00 | 15.17 | 19.5 | −1.54 |
|  | (29.5) | (20.83) | (28.83) | (30.17) | (26.0) |

Tables 28-31 show PD parameters for Formulations 1-4 compared to Ref (arithmetic mean difference, 90% CI). Table 28 shows comparisons for systolic blood pressure (SBP), Table 29 for diastolic blood pressure (DBP), Table 30 for mean arterial blood pressure (MAP), and Table 31 for heart rate (HR).

TABLE 28

| Comparison | AUECt | AUEC20 | AUEC45 | AUEC90 | Emax | Emin |
|---|---|---|---|---|---|---|
| 1:Ref | 33.60 | 2.39 | 6.40 | 12.91 | 7.43 | 4.16 |
|  | (22.26, 44.95) | (1.54, 3.24) | (4.63, 8.17) | (9.81, 16.01) | (4.38, 10.48) | (2.09, 6.23) |
| 2:Ref | 29.99 | 2.24 | 6.11 | 11.70 | 8.06 | 4.69 |
|  | (18.76, 41.22) | (1.40, 3.08) | (4.35, 7.86) | (8.64, 14.76) | (5.04, 11.08) | (2.64, 6.73) |
| 3:Ref | 32.77 | 2.52 | 6.00 | 11.59 | 7.31 | 3.80 |
|  | (21.53, 44.01) | (1.67, 3.36) | (4.25, 7.76) | (8.53, 14.66) | (4.29, 10.33) | (1.75, 5.84) |
| 4:Ref | 33.53 | 2.48 | 6.32 | 12.88 | 9.52 | 2.99 |
|  | (22.33, 44.72) | (1.65, 3.32) | (4.58, 8.07) | (9.82, 15.93) | (6.51, 12.53) | (0.95, 5.03) |

TABLE 29

| Comparison | AUECt | AUEC20 | AUEC45 | AUEC90 | Emax | Emin |
|---|---|---|---|---|---|---|
| 1:Ref | 24.25 | 2.19 | 5.25 | 9.89 | 7.94 | 3.91 |
|  | (15.63, 32.86) | (1.63, 2.76) | (4.01, 6.50) | (7.46, 12.32) | (5.03, 10.86) | (2.25, 5.57) |
| 2:Ref | 20.26 | 1.94 | 4.35 | 7.76 | 6.69 | 4.08 |
|  | (11.73, 28.79) | (1.39, 2.50) | (3.12, 5.58) | (5.36, 10.17) | (3.81, 9.57) | (2.43, 5.72) |
| 3:Ref | 20.43 | 1.95 | 4.33 | 7.75 | 5.7 | 4.16 |
|  | (11.90, 28.96) | (1.39, 2.51) | (3.10, 5.56) | (5.34, 10.16) | (2.82, 8.58) | (2.52, 5.81) |
| 4:Ref | 17.41 | 1.91 | 4.42 | 8.58 | 6.34 | 3.12 |
|  | (8.91, 25.91) | (1.35, 2.46) | (3.19, 5.64) | (6.18, 10.98) | (3.47, 9.21) | (1.48, 4.76) |

TABLE 30

| Comparison | AUECt | AUEC20 | AUEC45 | AUEC90 | Emax | Emin |
|---|---|---|---|---|---|---|
| 1:Ref | 27.37 | 2.26 | 5.64 | 10.90 | 7.70 | 3.62 |
|  | (18.86, 35.87) | (1.65, 2.86) | (4.32, 6.95) | (8.45, 13.35) | (4.96, 10.45) | (2.07, 5.17) |

TABLE 30-continued

| Comparison | AUECt | AUEC20 | AUEC45 | AUEC90 | Emax | Emin |
|---|---|---|---|---|---|---|
| 2:Ref | 23.50 (15.08, 31.92) | 2.04 (1.44, 2.64) | 4.93 (3.63, 6.24) | 9.08 (6.65, 11.50) | 6.57 (3.85, 9.28) | 4.23 (2.69, 5.77) |
| 3:Ref | 24.54 (16.12, 32.97) | 2.14 (1.54, 2.74) | 4.89 (3.58, 6.19) | 9.03 (6.60, 11.46) | 6.11 (3.40, 8.83) | 3.81 (2.27, 5.35) |
| 4:Ref | 22.79 (14.40, 31.18) | 2.10 (1.50, 2.70) | 5.05 (3.75, 6.35) | 10.01 (7.60, 12.43) | 7.27 (4.56, 9.98) | 2.88 (1.35, 4.42) |

TABLE 31

| Comparison | AUECt | AUEC20 | AUEC45 | AUEC90 | Emax | Emin |
|---|---|---|---|---|---|---|
| 1:Ref | 17.67 (8.29, 27.05) | 0.91 (0.38, 1.44) | 1.77 (0.52, 3.02) | 3.70 (1.16, 6.24) | 1.09 (−1.33, 3.52) | 1.98 (0.40, 3.56) |
| 2:Ref | 8.15 (−1.13, 17.43) | 0.74 (0.21, 1.26) | 1.24 (0.01, 2.48) | 2.79 (0.27, 5.31) | 1.19 (−1.20, 3.59) | 0.80 (−0.76, 2.36) |
| 3:Ref | 16.18 (6.90, 25.47) | 0.89 (0.36, 1.42) | 1.88 (0.64, 3.12) | 4.10 (1.59, 6.62) | 2.07 (−0.32, 4.47) | 1.53 (−0.03, 3.09) |
| 4:Ref | 20.71 (11.47, 29.96) | 1.31 (0.79, 1.83) | 2.56 (1.33, 3.79) | 5.35 (2.84, 7.86) | 4.29 (1.91, 6.68) | 2.18 (0.62, 3.74) |

For SPB, DBP and MAP (Tables 28-30), the AUEC parameters and Emax were significantly higher for all IMPs compared to Ref (90% CI>0). For HR (Table 31), most IMPs had higher AUEC parameters compared to Ref, and there was a trend towards a higher Emax as well.

All epinephrine nasal powder formulations (1-4), had higher total exposure of epinephrine (AUC(t)) than Ref and similar or higher Cmax compared to Ref. Tmax was somewhat lower than Ref for Formulations 1-4, but as shown in Table 23, after 20 min, all four epinephrine nasal powder formulations had similar or higher epinephrine exposure than Ref.

Nasal administration of epinephrine nasal powder was considered to be safe, with no severe adverse events (AEs) being reported in the trial. The most commonly reported AEs were nasal discomfort, rhinalgia, headache and palpitations.

The invention claimed is:

1. A method of treatment of an allergic reaction, which method comprises:
administering a powder composition from a needle-free intranasal applicator to a patient suffering from, or susceptible to, said allergic reaction, which applicator is suitable for administering said powder composition into a nostril of a human patient, wherein the applicator comprises:
(i) an opaque reservoir comprising said powder composition; and
(ii) an outlet through which, following actuation, said powder composition may be dispensed,
wherein said powder composition comprises a pharmacologically-effective dosage amount of epinephrine (adrenaline), or a pharmaceutically-acceptable salt thereof, as the sole active ingredient, and wherein said powder composition comprises a composite material in powder form, which composite material includes the epinephrine or salt thereof and a pharmaceutically-acceptable carrier material, wherein the epinephrine or salt thereof and the pharmaceutically-acceptable carrier material are presented together within single amorphous particles; and
which powder composition is essentially free of water and wherein the epinephrine or salt thereof is less than about 4% chemically degraded after storage of the powder composition for:
(a) at least about 3 months at 40° C. and 75% relative humidity; and/or
(b) at least about 18 months at below about 30° C.; and/or
(c) at least about 18 hours at above about 1 million lux of UV light.

2. A method of treatment of an allergic reaction, which method comprises:
(a) providing a needle-free, nasal applicator device in a container that substantially prevents ingress of atmospheric water by comprising thermoformed plastics and/or molecular sieves with a pore size of 3 Å or 4 Å, wherein the applicator device comprises (i) an opaque reservoir comprising a powder composition, and (ii) an outlet through which said powder composition may be dispensed upon actuation, wherein said powder composition comprises a pharmacologically-effective dosage amount of epinephrine (adrenaline), or a pharmaceutically-acceptable salt thereof, as the sole active ingredient, and wherein said powder composition comprises a composite material in powder form, which composite material includes the epinephrine or salt thereof and a pharmaceutically-acceptable carrier material, wherein the epinephrine or salt thereof and the pharmaceutically-acceptable carrier material are presented together within single amorphous particles, which powder composition is essentially free of water and wherein the epinephrine or salt thereof is less than about 4% chemically degraded after storage of the powder composition for:

at least about 3 months at 40° C. and 75% relative humidity, and/or at least about 18 months at below about 30° C., and/or at least about 18 hours at above about 1 million lux of UV light;

(b) removing the nasal applicator device from the container; and (c) actuating the nasal applicator device to deposit an effective dose of epinephrine, or salt thereof, to the nasal mucosa of a patient suffering from, or susceptible to, the allergic reaction.

3. A method of treatment of an allergic reaction in a human patient, which comprises:

(A) providing a needle-free, nasal applicator device in a container that substantially prevents ingress of atmospheric water by comprising thermoformed plastics and/or molecular sieves with a pore size of 3 Å or 4 Å, wherein the applicator device comprises (i) an opaque reservoir comprising a powder composition, and (ii) an outlet through which said powder composition may be dispensed upon actuation, wherein said powder composition comprises a pharmacologically-effective dosage amount of epinephrine (adrenaline), or a pharmaceutically-acceptable salt thereof, as the sole active ingredient, and wherein said powder composition comprises a composite material in powder form, which composite material includes the epinephrine or salt thereof and a pharmaceutically-acceptable carrier material, wherein the epinephrine or salt thereof and the pharmaceutically-acceptable carrier material are presented together within single amorphous particles, which powder composition is essentially free of water and wherein the epinephrine or salt thereof is less than about 4% chemically degraded after storage of the powder composition for:

at least about 3 months at 40° C. and 75% relative humidity, and/or at least about 18 months at below about 30° C., and/or at least about 18 hours at above about 1 million lux of UV light;

(B) identifying a human patient that is, or is in acute danger of, having such an allergic reaction; and (C) administering a dosage amount of epinephrine (adrenaline), or a pharmaceutically-acceptable salt thereof, from the needle-free applicator by actuating said applicator to dispense said dosage amount of epinephrine or salt thereof into a nasal cavity of said patient, thereby presenting the powder composition comprising said epinephrine or salt thereof at nasal mucosa to facilitate absorption of said epinephrine across said nasal mucosa, and treating said allergic reaction.

4. The method as claimed in claim 3, wherein the administering step is carried out immediately after the identification step.

5. The method as claimed in claim 4, wherein the administering step is carried out without:

(i) inspecting the composition contained within the reservoir of the applicator; and (ii) ascertaining whether the relevant composition may be safely administered to the patient to treat said allergic reaction effectively.

6. The method as claimed in claim 1, wherein the allergic reaction comprises anaphylaxis.

7. The method as claimed in claim 6, wherein the anaphylaxis results from a reaction to an insect sting or bite, a foodstuff or a drug and/or another chemical substance.

8. The method as claimed in claim 6 wherein the anaphylaxis is idiopathic anaphylaxis or exercise-induced anaphylaxis.

9. The method as claimed in claim 1, wherein the pharmaceutically-acceptable carrier material of the powder composition comprises a maltodextrin.

10. The method as claimed in claim 9, wherein the maltodextrin comprises maltodextrin 19DE.

11. The method as claimed in claim 1, wherein the pharmaceutically-acceptable carrier material of the powder composition comprises a disaccharide selected from the group consisting of maltitol, trehalose, sucralose, sucrose, isomalt, maltose and lactose.

12. The method as claimed in claim 11, wherein the disaccharide comprises lactose or trehalose.

13. The method as claimed in claim 1, wherein the carrier material of the powder composition comprises a combination of trehalose and maltodextrin 19DE.

14. The method as claimed in claim 13, wherein the ratio of trehalose:maltodextrin by weight is in the range of about 10:1 to about 1:20.

15. The method as claimed in claim 13, wherein the ratio of trehalose:maltodextrin by weight is in the range of about 2:1 to about 1:8.

16. The method as claimed in claim 1, wherein the lowest measurable glass transition temperature of the powder composition is at least about 35° C. when measured at a relative humidity of up to about 35%.

17. The method as claimed in claim 1, wherein the powder composition further comprises a sucrose ester.

18. The method as claimed in claim 17, wherein the sucrose ester comprises sucrose monolaurate.

19. The method as claimed in claim 1, wherein the particle size distribution of said powder composition includes:

(a) a D10 that is above about 3 µm; and/or (b) a volume-based mean diameter within the range of about 10 µm and about 100 µm.

20. The method as claimed in claim 1, wherein the particle size distribution of said powder composition includes:

(a) a D10 above about 10 µm; and (b) a D90 below about 500 µm.

21. The method as claimed in claim 20, wherein the D90 is below about 100 µm.

22. The method as claimed in claim 1, wherein the pharmacologically-effective dosage amount of epinephrine is between about 0.5 mg and about 3 mg (calculated as the free base).

23. The method as claimed in claim 1, wherein the applicator comprises an actuator that generates a dispensing force upon actuation of the device by a user.

24. The method as claimed in claim 23, wherein the applicator is configured such that, upon actuation, said powder composition is dispensed, thereby depositing a pharmacologically-effective dosage of said epinephrine or salt thereof, to the nasal mucosa.

25. A method of treatment of an allergic reaction, which method comprises the administration of a powder composition from a needle-free applicator that is suitable for administering said powder composition comprising pharmacologically-effective dosage amount of epinephrine (adrenaline), or a pharmaceutically-acceptable salt thereof, into a human nostril, wherein said applicator comprises:

(i) an opaque reservoir containing said powder composition;

(ii) an actuator that generates a dispensing force upon actuation of the device by a user; and (iii) an outlet through which, upon actuation, said powder composition is dispensed, thereby depositing a pharmacologically-effective dosage amount epinephrine or salt thereof to the nasal mucosa, wherein the powder composition contained in said reservoir is a spray-dried composite material in powder form, which composite material includes the epinephrine or pharmaceutically-acceptable salt thereof, sucrose monolaurate, and a pharmaceutically-acceptable carrier material, wherein the epinephrine or salt thereof, sucrose monolaurate, and the pharmaceutically-acceptable carrier material are presented together within single amorphous particles, and wherein the powder composition comprises:

(1) about 0.5 mg to about 2 mg (calculated as the free base) of epinephrine or pharmaceutically-acceptable salt thereof as the sole active ingredient;

(2) a combination of trehalose and maltodextrin 19DE, in a ratio of between about 3:1 and 1:3 by weight, as the pharmaceutically-acceptable carrier material;

(3) about 0.75% to about 3% by weight of the sucrose monolaurate; and (4) less than about 5% of water, wherein the particle size distribution of the powder comprises a D10 above about 10 µm and a D90 below about 100 µm, and wherein the epinephrine or salt thereof is less than about 4% chemically degraded after storage of the powder composition for:

(a) at least about 3 months at 40° C. and 75% relative humidity; and/or (b) at least about 18 months at below about 30° C.; and/or (c) at least about 18 hours at above about 1 million lux of UV light.

26. The method as claimed in claim 25, wherein the applicator is packaged within a container that substantially prevents the ingress of atmospheric water.

27. The method as claimed in claim 26, wherein the container comprises a material selected from the group: heat-sealed aluminium pouches and thermoformed plastics and/or a desiccant selected from the group: silica gel and molecular sieves with a pore size of 3 Å or 4 Å.

28. The method as claimed in claim 1, wherein said composite material is a spray-dried composite material in powder form.

29. The method as claimed in claim 2, wherein said composite material is a spray-dried composite material in powder form.

30. The method as claimed in claim 3, wherein said composite material is a spray-dried composite material in powder form.

* * * * *